(12) United States Patent
DeVries et al.

(10) Patent No.: US 9,226,652 B2
(45) Date of Patent: Jan. 5, 2016

(54) DEVICES AND METHODS FOR TISSUE INVAGINATION

(75) Inventors: Robert B. DeVries, Northborough, MA (US); Roy H. Sullivan, Millville, MA (US); Marc Tassy, Jr., Framingham, MA (US); Kristian DiMatteo, Waltham, MA (US); Tak Kwan, Medford, MA (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 967 days.

(21) Appl. No.: 13/176,172

(22) Filed: Jul. 5, 2011

(65) Prior Publication Data

US 2012/0004505 A1 Jan. 5, 2012

Related U.S. Application Data

(63) Continuation of application No. 11/347,249, filed on Feb. 6, 2006, now abandoned, which is a continuation of application No. 10/748,243, filed on Dec. 31, 2003, now abandoned.

(51) Int. Cl.
| | |
|---|---|
| *A61M 5/00* | (2006.01) |
| *A61M 25/00* | (2006.01) |
| *A61B 1/00* | (2006.01) |
| *A61B 1/04* | (2006.01) |
| *A61B 1/32* | (2006.01) |
| *A61B 17/00* | (2006.01) |
| *A61B 17/02* | (2006.01) |
| *A61B 17/04* | (2006.01) |
| *A61B 17/128* | (2006.01) |
| *A61B 17/11* | (2006.01) |
| *A61B 17/29* | (2006.01) |
| *A61B 17/30* | (2006.01) |

(52) U.S. Cl.
CPC ............ *A61B 1/32* (2013.01); *A61B 17/00234* (2013.01); *A61B 17/0218* (2013.01); *A61B 17/0469* (2013.01); *A61B 17/1285* (2013.01); *A61B 17/1114* (2013.01); *A61B 17/29* (2013.01); *A61B 2017/00336* (2013.01); *A61B 2017/00557* (2013.01); *A61B 2017/00827* (2013.01); *A61B 2017/0419* (2013.01); *A61B 2017/306* (2013.01); *A61B 2017/308* (2013.01)

(58) Field of Classification Search
USPC ......... 600/104, 106, 107, 114–116, 127, 129, 600/121–125; 604/171–172, 96.01, 101, 1, 604/101.02, 101.03, 101.04, 101.05, 604/102.01, 102.02, 102.03, 103, 103.03, 604/103.04, 103.05, 103.06, 103.07, 604/103.08, 263, 264, 271; 606/140
See application file for complete search history.

(56) References Cited

U.S. PATENT DOCUMENTS

| | | | | |
|---|---|---|---|---|
| 5,176,687 | A * | 1/1993 | Hasson et al. | 606/114 |
| 5,454,789 | A * | 10/1995 | Burns et al. | 604/99.04 |
| 5,490,837 | A * | 2/1996 | Blaeser et al. | 604/103.11 |

(Continued)

*Primary Examiner* — Ryan Henderson
(74) *Attorney, Agent, or Firm* — Bookoff McAndrews, PLLC

(57) ABSTRACT

Surgical devices and methods used for invaginating tissue during, for example, an endoscopic fundoplication procedure, are disclosed. The device includes an elongated tube having a proximal end configured to extend outside of the body and a distal end configured to extend proximate the tissue to be invaginated, and a distal member coupled to the distal end of the tube. The distal member is configured to hold or grasp the tissue to be invaginated. The devices may include a protective distal sleeve.

19 Claims, 34 Drawing Sheets

(56) References Cited

U.S. PATENT DOCUMENTS

| | | | |
|---|---|---|---|
| 5,624,453 A * | 4/1997 | Ahmed | 606/140 |
| 5,857,585 A * | 1/1999 | Tolkoff et al. | 221/36 |
| 6,051,003 A * | 4/2000 | Chu et al. | 606/140 |
| 6,306,081 B1 * | 10/2001 | Ishikawa et al. | 600/127 |
| 6,869,393 B2 * | 3/2005 | Butler | 600/114 |
| 2007/0260112 A1 * | 11/2007 | Rahmani | 600/104 |
| 2009/0156998 A1 * | 6/2009 | Arana et al. | 604/103 |

* cited by examiner

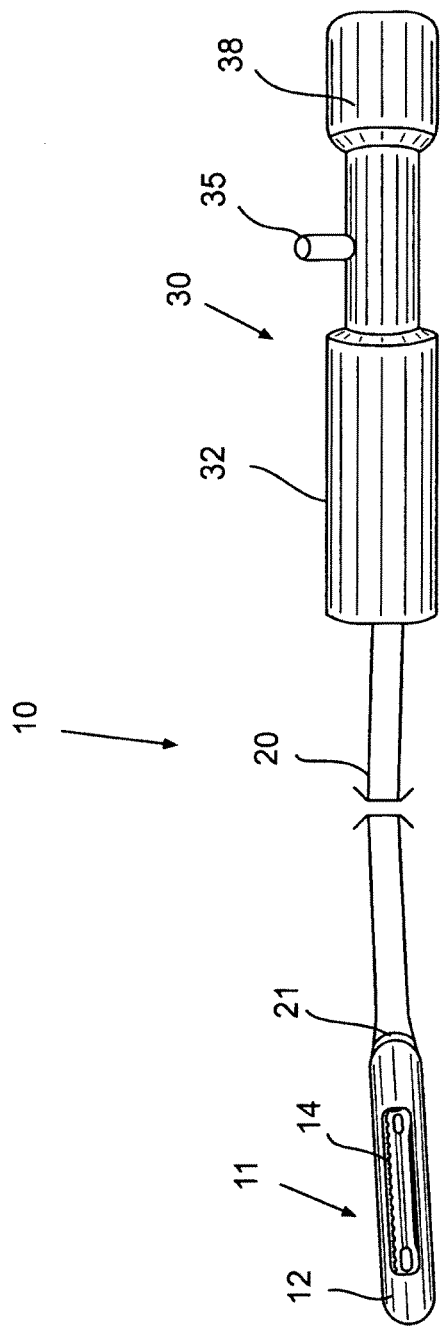
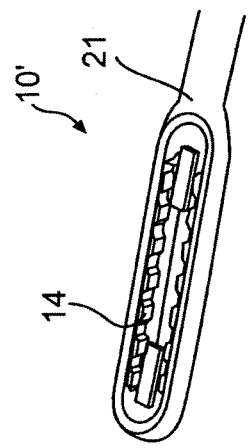
FIG. 4
FIG. 5

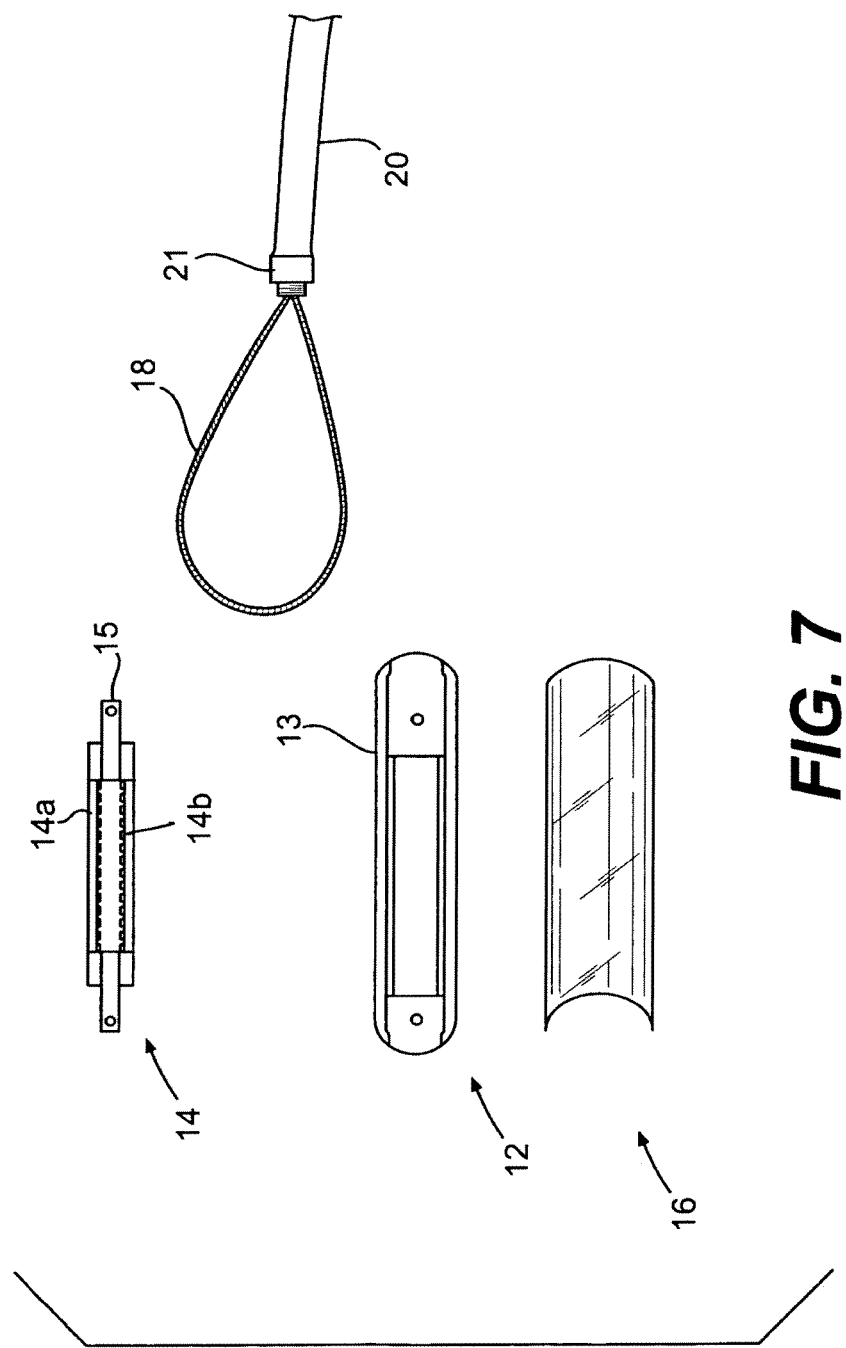

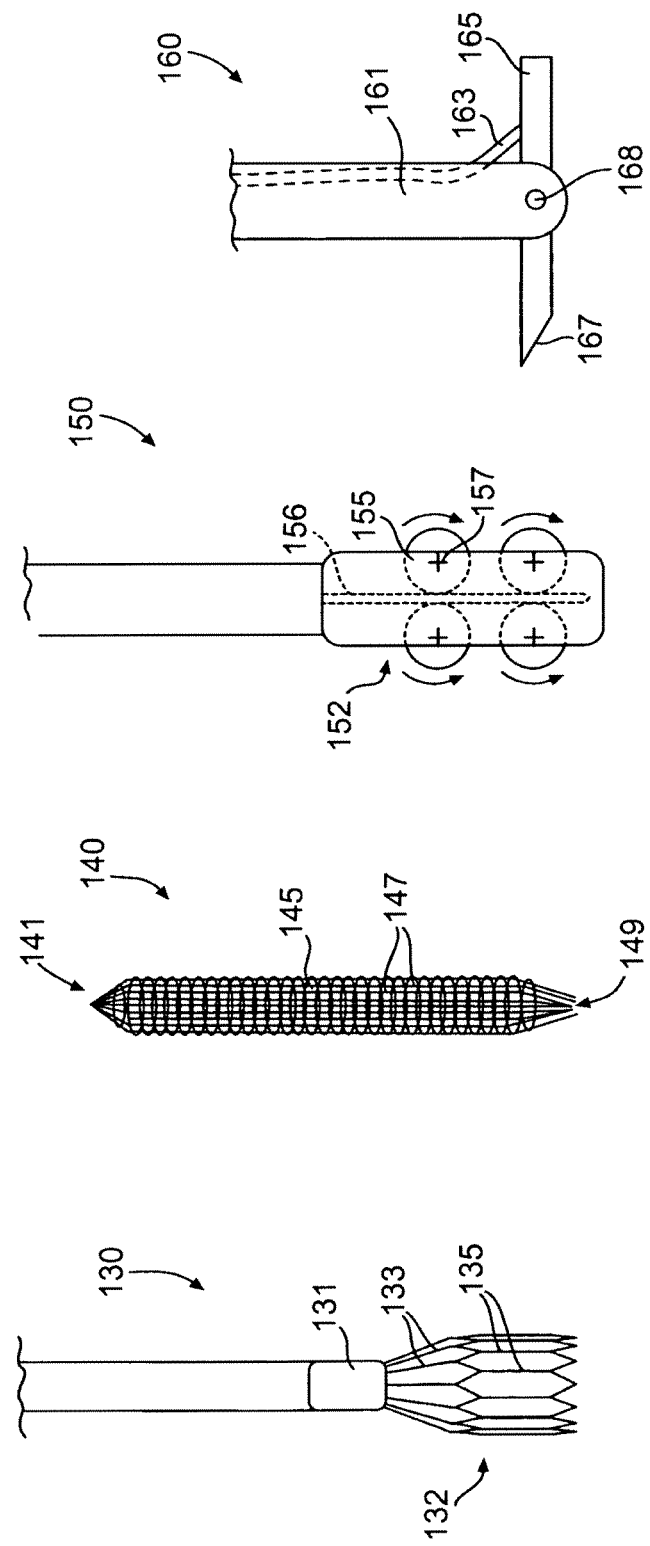

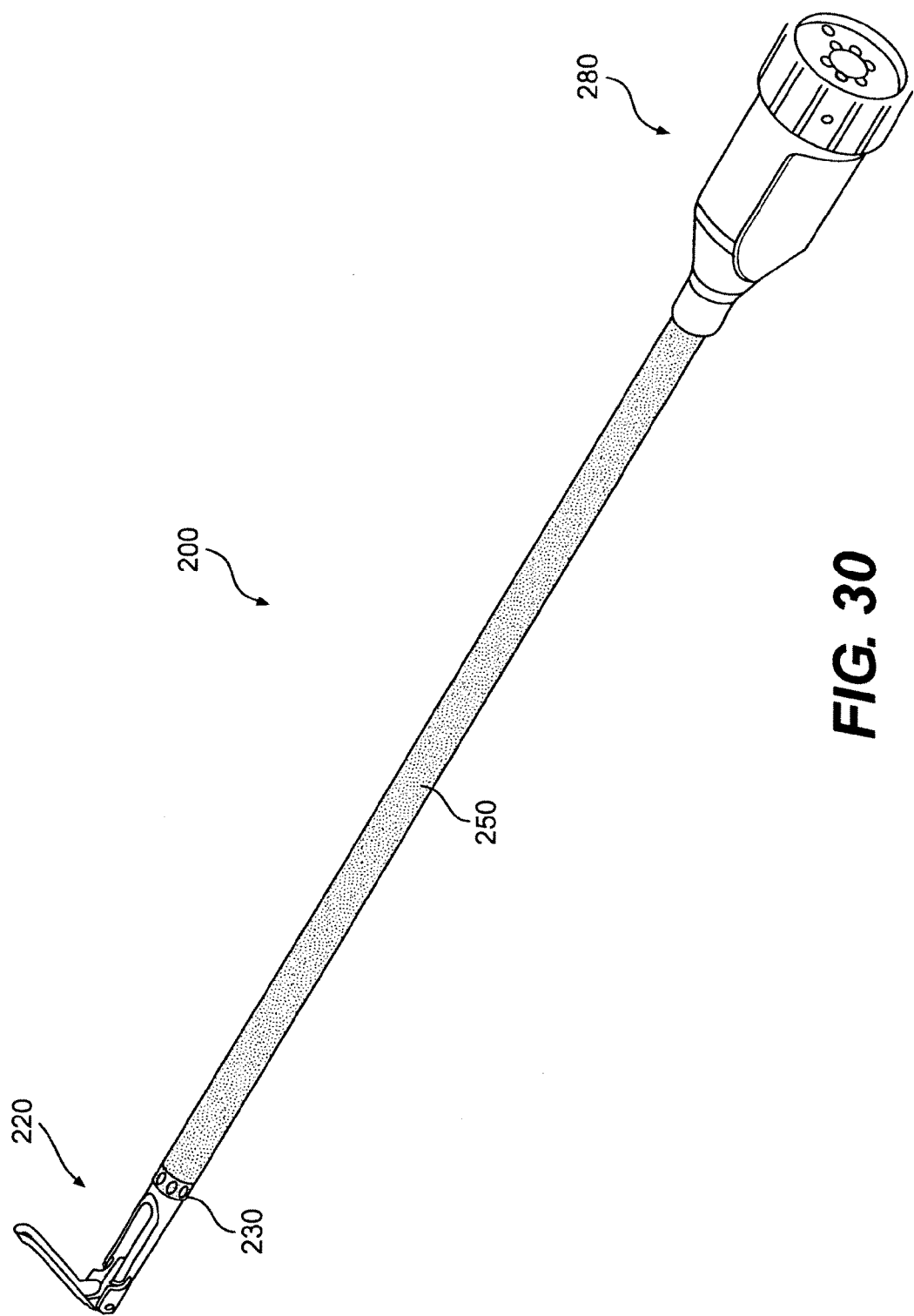

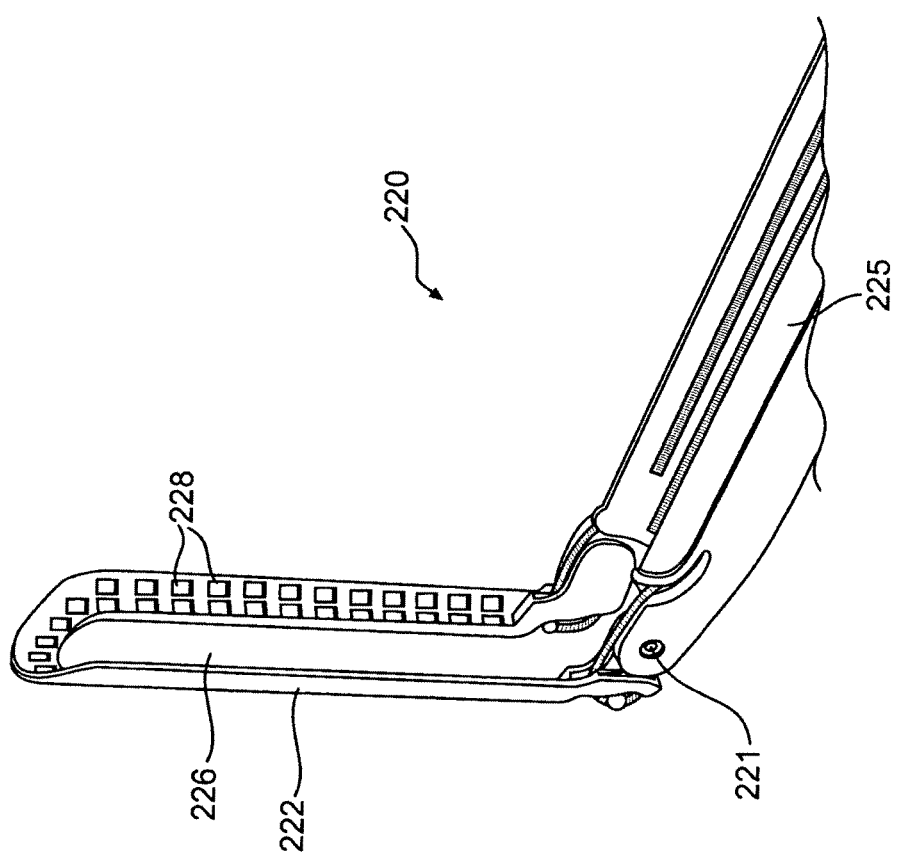

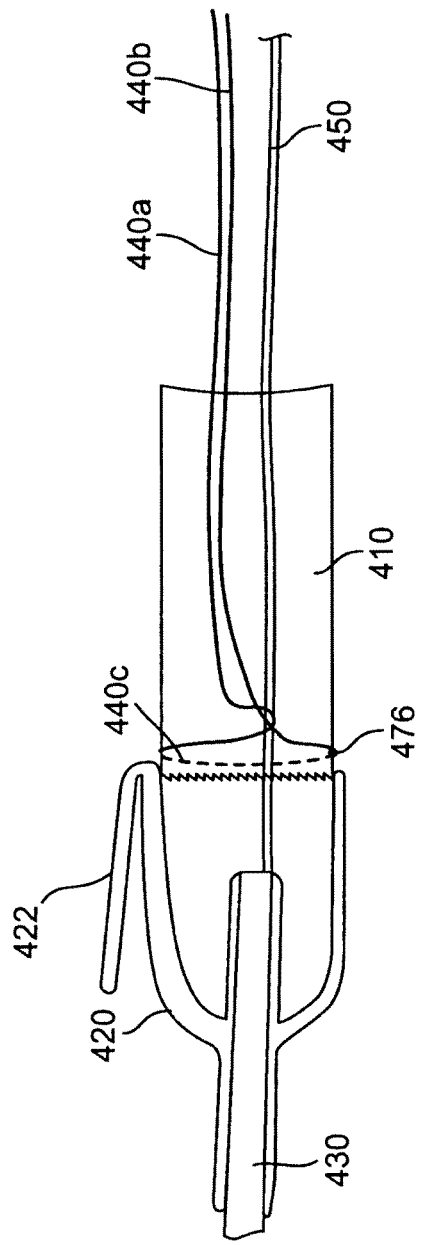

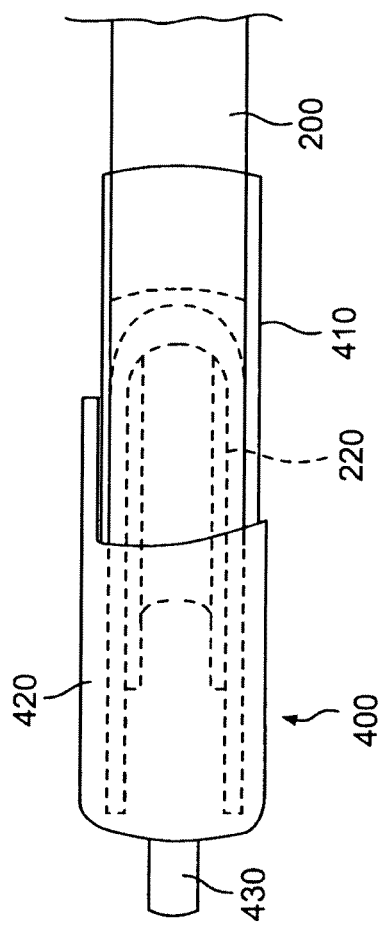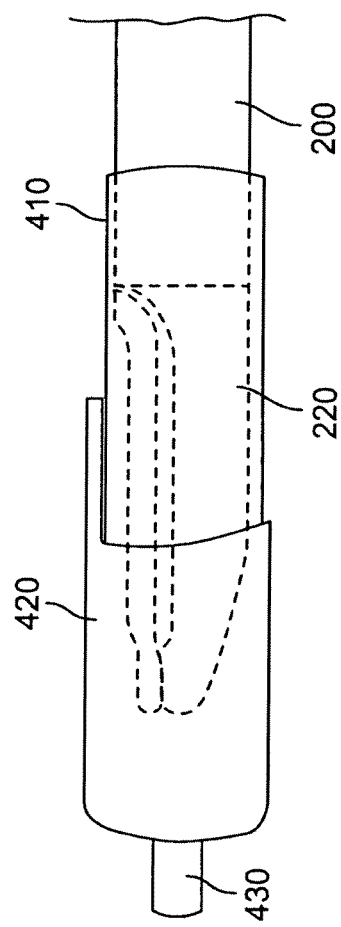

DEVICES AND METHODS FOR TISSUE INVAGINATION

CROSS-REFERENCE TO RELATED APPLICATIONS

This application is a continuation of application Ser. No. 11/347,249, filed Feb. 6, 2006 now abandoned, which is a continuation of abandoned application Ser. No. 10/748,243, filed Dec. 31, 2003, both of which are incorporated herein by reference.

FIELD OF THE INVENTION

The present invention relates to endoscopic devices and related methods. In particular, the present invention relates to endoscopic devices and methods used in, for example, a tissue invagination procedure for treatment of Gastroesophageal Reflux Disease (GERD).

BACKGROUND OF THE INVENTION

Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES). With reference to FIG. 1, the LES 2 is a ring of smooth muscle and increased annular thickness existing in approximately the last four centimeters of the esophagus. In its resting state, the LES creates a region of high pressure (approximately 15-30 mm Hg above intragastric pressure) at the opening of the esophagus 3 into the stomach 7. This pressure essentially closes the esophagus 3 so that contents of the stomach cannot pass back into the esophagus 3. The LES 2 opens in response to swallowing and peristaltic motion in the esophagus, allowing food to pass into the stomach. After opening, however, a properly functioning LES 2 should return to the resting, or closed state. Transient relaxations of the LES 2 do occur in healthy individuals, typically resulting in occasional bouts of heartburn.

The physical interaction occurring between the gastric fundus 5 and the esophagus 3 also prevents gastroesophageal reflux. The gastric fundus 5 is a lobe of the stomach situated at the top of the stomach 7 distal to the esophagus 3. In asymptomatic individuals, the fundus 5 presses against the opening of the esophagus 3 when the stomach 7 is full of food and/or gas. This effectively closes off the esophageal opening to the stomach 7 and helps to prevent acid reflux back into the esophagus 3. More specifically, as the food bolus is immersed in gastric acid, it releases gas which causes the fundus 5 of the stomach 7 to expand and thereby exert pressure on the distal esophagus 3 causing it to collapse. The collapse of the esophagus lumen reduces the space for the stomach acid to splash past the closed esophagus lumen and thereby protect the proximal esophagus from its destructive contact.

In individuals with GERD, the LES 2 functions abnormally, either due to an increase in transient LES relaxations, decreased muscle tone of the LES 2 during resting, or an inability of the esophageal tissue to resist injury or repair itself after injury. These conditions often are exacerbated by overeating, intake of caffeine, chocolate or fatty foods, smoking, and/or hiatal hernia. Avoiding these exacerbating mechanisms helps curb the negative side effects associated with GERD, but does not change the underlying disease mechanism.

A surgical procedure, known generally as fundoplication, has been developed to prevent acid reflux in patients whose normal LES functioning has been impaired, either as a result of GERD or other adverse effects. This procedure involves bringing the fundus wall 6 into closer proximity of the esophageal wall 4 to help close off the esophageal opening into the stomach 7, as shown in FIG. 2. Traditionally, this procedure has been performed as an open surgery, but also has been performed laparoscopically.

As with any surgery, the attendant risks are great. Due to relatively large incisions necessary in the performance of open surgery, relatively large amount of blood is lost, the risk of infection increases, and the potential for post-operative hernias is high. Further, the relatively large incisions necessary in the performance of open surgery require extended recovery times for the incision to heal.

A laparoscopic procedure may involve performing laparotomies for trocar ports (penetrations of the abdominal wall), percutaneous endoscopic gastronomies (incisions through the skin into the stomach), and the installation of ports through which, for example, a stapler, an endoscope, and an esophageal manipulator (invagination device) are inserted. Under view of the endoscope, an esophageal manipulator is used to pull the interior of the esophagus 3 into the stomach 7. When the esophagus is in position, with the fundus 5 of the stomach plicated, the stapler is moved into position around the lower end of the esophagus and the plicated fundus is stapled to the esophagus 3. The process may be repeated at different axial and rotary positions until the desired fundoplication is achieved. This procedure is still relatively invasive requiring incisions through the stomach, which has a risk of infection. The location of the incision in the abdominal wall presents a risk of other negative effects, such as sepsis, which can be caused by leakage of septic fluid contained in the stomach.

SUMMARY OF THE INVENTION

Therefore, it is accordingly an object of the present invention to provide less invasive devices and methods for performing the fundoplication procedure. This is achieved by using an invagination device which can be endoluminally delivered through the esophagus, thereby eliminating the need for highly invasive, physiologically insulting surgical procedures.

To attain the advantages and in accordance with the purpose of the invention, as embodied and broadly described herein, one aspect of the invention provides a surgical device for holding esophageal tissue during a fundoplication procedure. The device includes a proximal member having a vacuum port connectable to a source of vacuum, a substantially flexible conduit having a proximal end connected to the proximal member and a lumen in fluid communication with the source of vacuum, and a distal member connected to a distal end of the conduit and configured to hold the esophageal tissue when suction is supplied to the vacuum port from the source of vacuum.

Another aspect of the present invention is to provide a surgical device for invaginating esophageal tissue of a body. The device includes an elongated tube having a proximal end configured to extend outside of the body and a distal end configured to extend proximate the esophageal tissue of the body, and a distal member coupled to the distal end of the tube. The distal member further includes a friction member for frictionally engaging the esophageal tissue.

In yet another aspect of the present invention, a surgical device for invaginating tissue of a first organ into a second organ in a body is provided. The device includes an elongated tube having a proximal end configured to extend outside of the body and a distal end configured to extend proximate the tissue of the first organ, and a distal member coupled to the distal end of the tube and configured to extend beyond the tissue to be invaginated and into the second organ. The distal member further includes an expandable portion for applying a force to tissue of the second organ and thereby invaginate the tissue of the first organ into the second organ.

In still another aspect of the present invention, a device for displacing tissue of a body is provided. The device includes an elongated tube having a proximal end configured to extend outside of the body and a distal end configured to extend proximate the tissue, and a distal member coupled to the distal end of the tube and having at least one rotating member. The rotating member is configured to contact the tissue layer and displace the tissue in the rotating direction.

In still another aspect of the present invention, a surgical device for displacing tissue of a body is provided. The device includes an elongated tube having a proximal end configured to extend outside of the body and a distal end configured to extend proximate the tissue, and a distal member coupled to the distal end of the tube and having a rotatable arm configured to rotate relative to the axis of the tube. At least one end of the rotatable arm is configured to contact the tissue when the rotatable arm rotates relative to the axis of the tube.

In still another aspect of the present invention, a device for grasping tissue of a body is provided. The device includes an elongated tube having a proximal end configured to extend outside of the body and a distal end configured to extend proximate the tissue, and a distal member coupled to the distal end of the tube and having a plurality of legs each configured to extend radially outwardly in an expanded state and engage the tissue.

In still another aspect of the present invention, a surgical device for grasping esophageal tissue of a body is provided. The device includes a flexible elongated tube having a proximal end configured to extend outside of the body and a distal end configured to extend proximate the esophageal tissue of the body, and a distal member coupled to the distal end of the tube and having at least one forceps to grasp the esophageal tissue.

In still another aspect of the present invention, a method of invaginating tissue toward an organ having an opening is provided. The method includes inserting an elongated tubular member into a body passage so that a distal end of the tubular member is proximate the tissue, contacting the tissue with the distal end, and displacing the tissue toward the opening of the organ by displacing the distal end of the member.

In another aspect of the present invention, a device to cover a distal end of an endoscopic instrument includes a distal tube having a lumen sized to receive an endoscope, an inflatable member coupled to the distal tube, a sleeve configured to cover the distal end of the endoscopic instrument, the inflatable member covering a distal end of the sleeve, and a tube having an inflation lumen in fluid communication with the inflatable member.

In another aspect of the present invention, a method of inserting an endoscopic instrument into a tissue tract of a patient includes placing a protective device over a distal end of the endoscopic instrument, the protective device including a sleeve to cover the distal end of the endoscopic instrument and an inflatable member covering a distal end of the sleeve, inflating the inflatable member, and inserting the endoscopic instrument into the tissue tract of the patient with the inflatable member inflated.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

In the drawings:

FIGS. 4 and 5 are perspective views of an invagination device, according to an embodiment of the present invention;

FIGS. 6 and 7 are top and bottom views, respectively, of the invagination head shown in FIGS. 4 and 5, showing various components;

FIGS. 14-29 are perspective views of invagination devices, according to various embodiments of the present invention;

FIG. 30 is a perspective view of an A-frame device, according to an embodiment of the present invention;

FIG. 31C is a perspective view of the A-frame head, shown in FIGS. 31A-31B, with the folding arm in an open position;

FIGS. 41A-41D are side views of steps in the manufacture of the protective sleeve of FIG. 39, according to an embodiment of the present invention; and FIGS. 42A-42D are views of various steps in the use of the protective sleeve of FIG. 39 in an endoscopic procedure, according to an embodiment of the present invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1:
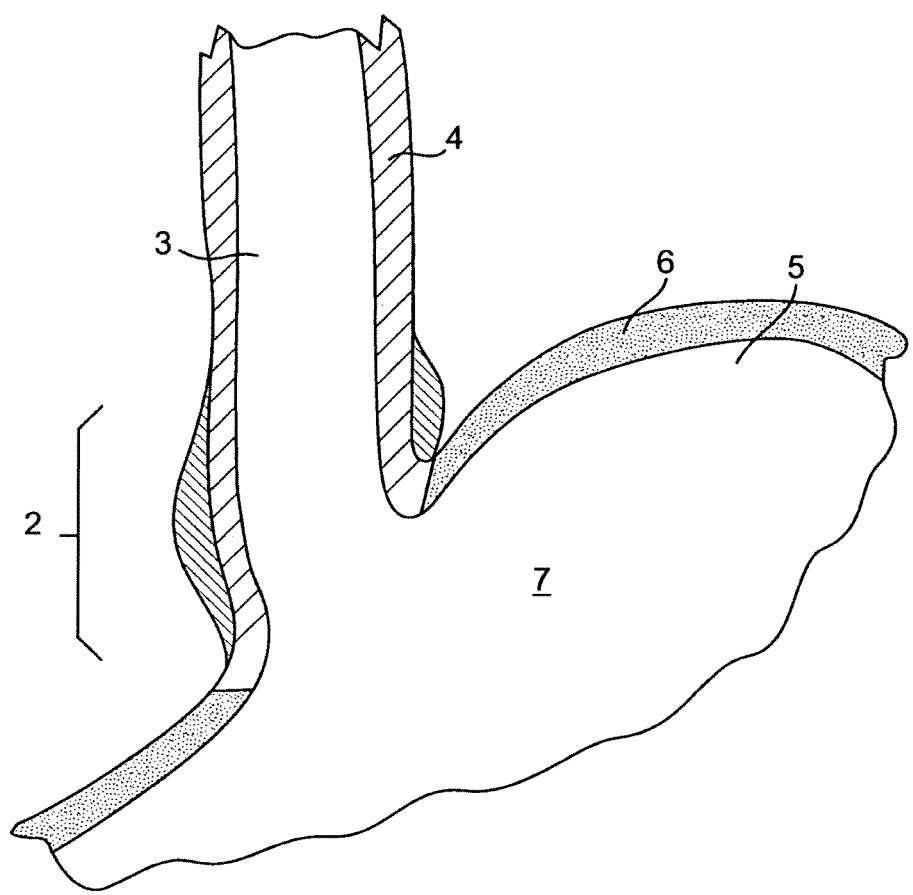
FIG. 1 is a cross-sectional view of the gastrointestinal tract in the region of the lower esophageal sphincter (LES) and the fundus of the stomach.
Figure 3:
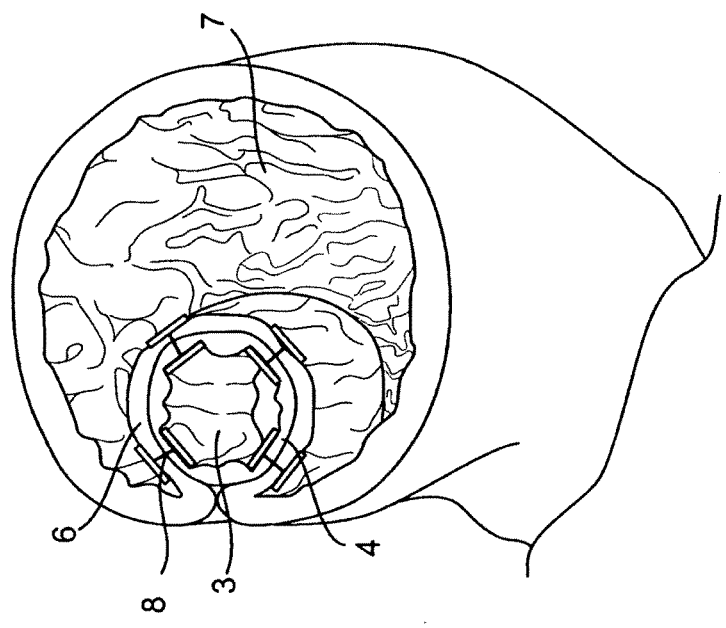
FIG. 3 is a perspective view of the gastrointestinal tract in the region of the lower esophageal sphincter (LES) and the fundus of the stomach, showing the cross-sectional view of the A-A' plane of FIG. 2 after a fundoplication procedure is performed.
Figure 2:
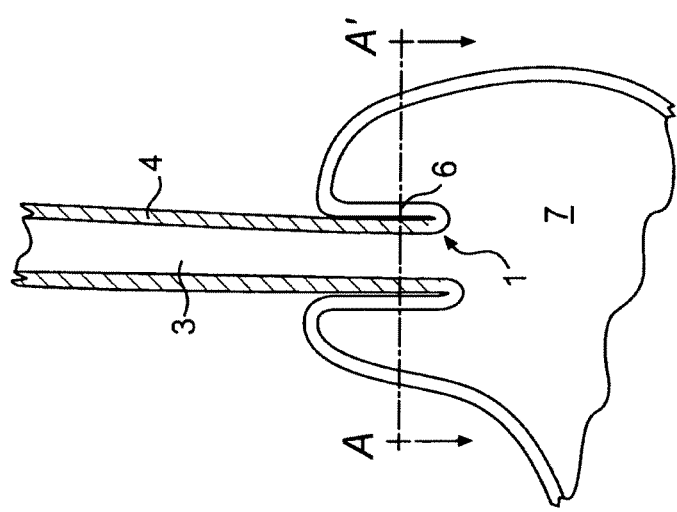
FIG. 2 is a cross-sectional view of the gastrointestinal tract in the region of the lower esophageal sphincter (LES) and the fundus of the stomach, after a fundoplication procedure is performed.

A newly developed form of fundoplication, referred to as endoscopic fundoplication, is an endoluminal procedure in which the fundus wall 6 is folded back onto the esophagus wall 4 and wraps around the esophagus 3, as shown in FIGS. 2 and 3. The tissue fold 1 formed between the esophagus 3 and the fundus 5 then is secured by suitable fastening means, such as, for example, a plurality of double T-fasteners 8. The endoscopic fundoplication can be performed by inserting required medical instruments through the esophagus 3. Such a procedure has the benefits of being less invasive, quicker, and less expensive as compared to previous techniques.

Various suitable tissue fasteners may be used, including adjustable fasteners that may be adjusted through various tools. Suitable fasteners are described in U.S. application Ser. No. 10/230,672 of Robert DeVries et al. entitled "Tissue Fasteners and Related Deployment Systems and Methods," U.S. application Ser. No. 10/175,307 of Sergey Grigoryants et al. entitled "Endoscopic Fundoplication Devices and Methods for Treatment of Gastroesophageal Reflux Disease," and U.S. application Ser. No. 10/230,682 of Robert DeVries et al. entitled "Devices and Methods for Fastening Tissue Layers." Each of these disclosures is incorporated by reference herein.

During an endoscopic fundoplication, an invagination device can be used to hold or grasp the esophagus wall 4 and pull it down toward the stomach 7 in order to invaginate the lower end portion of the esophagus 3 into the stomach. For example, when the fundus wall 6 is ready to be folded back onto the esophagus wall 4, an invagination device can be inserted through the esophagus 3 and positioned proximate to the lower end portion of the esophagus wall 4. Once the invagination device is properly positioned, the device is actuated to hold/grasp the tissue. After the portion of esophagus wall 4 is firmly held/grasped by the device, the device is pushed down toward the stomach to displace the held/grasped esophagus wall 4 down toward the stomach (e.g., approximately 4 cm). A suitable tissue fastening member is then used to securely fasten the invaginated esophagus wall 4 and the fundus wall 6. This invagination procedure may effectively eliminate a hiatal hernia that may protrude out of the stomach through the esophagus and recreate the LES region.

FIG. 4 shows an exemplary invagination device 10, according to an embodiment of the present invention. FIG. 5 shows a bottom view of the distal portion of the device 10. In this particular embodiment, the device 10 uses a suction mechanism to hold tissue to be invaginated. The device 10 includes an invagination head 11, an elongated conduit 20, and an actuation handle 30, as its main components. Each of these components is described further in detail.

Figure 6:
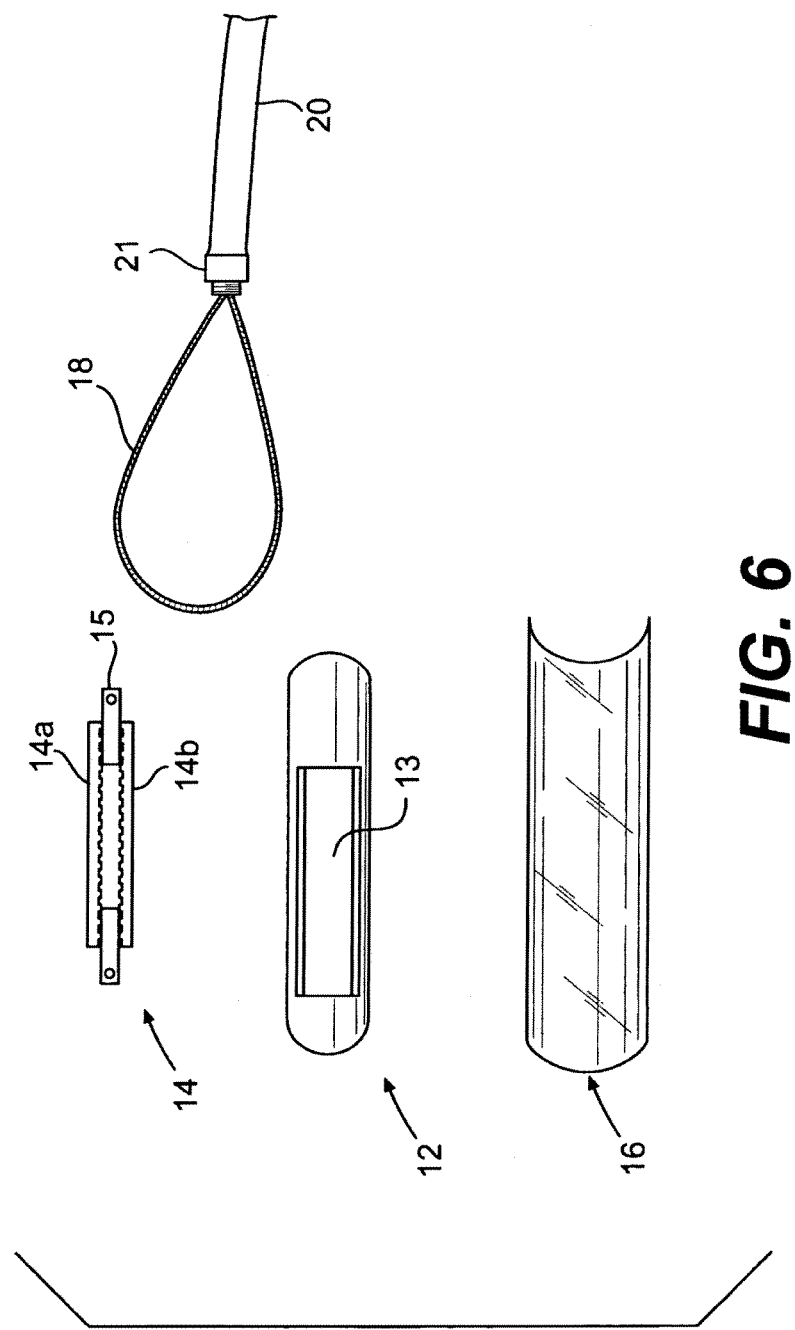
Figure 8A:
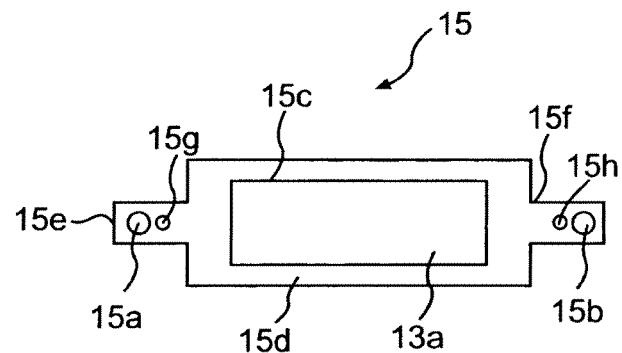
FIGS. 8A-B and 9A-B are schematic illustrations of various assembly stages of a jaw assembly, according to an embodiment of the present invention.
Figure 8B:
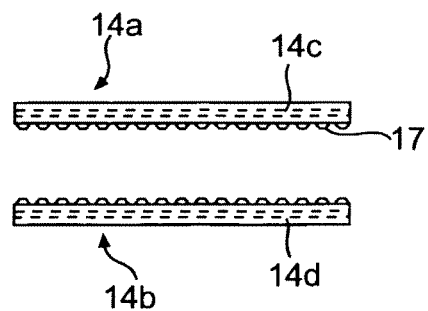

FIGS. 6 and 7 are top and bottom views of various elements of the invagination head 11. The head 11 includes a main body 12, a jaw assembly 14, a concave insert 16, and a jaw operating cable 18. The main body 12 has an opening 13 through which the tissue is to be held by suction. The jaw assembly 14 is disposed inside the opening 13 of the main body 12 to grasp the tissue more firmly once the tissue is held by suction. The main body 12 and the jaw assembly 14 can be made of metal, such as stainless steel or titanium, polymer, ceramic, or any other combination thereof. Body 12 and jaw 14 may also comprise any other biocompatible material known in the art. At least a portion of these components can be coated with a polymer or elastomer material to provide a softer contact and enhanced grip between the head 11 and the tissue to be invaginated. The concave insert 16, preferably made of a polymer or glass material, covers the back side of the invagination head 11 to form a suitable vacuum inside the invagination head 11, as shown in FIG. 5. The concave insert 16 can be translucent, so that the state of holding and grasping of the tissue can be readily observed from an endoscope.

FIGS. 8A, 8B, 9A, and 9B schematically illustrate various assembly stages of the jaw assembly 14. The jaw assembly 14 includes a pair of jaws 14a, 14b each of which has a plurality of teeth 17 facing each other. Each of the jaws 14a, 14b is fixedly attached to each side arm 15c, 15d of a spring set 15 by a suitable fixing mechanism, such as screws, welding, bonding, molding, or by any other connection means known in the art. The spring set 15 can be sufficiently flexible so that the side arms 15c, 15d of the spring set 15 can flex inward with respect to the central opening 13a to form a folded or deflected configuration, such as a U-shaped configuration, for example. As shown in FIG. 9, each of the jaws 14a, 14b forms a groove 14c, 14d (shown by dashed lines) in the surface facing the spring set 15. Once the jaws 14a, 14b are fixedly attached to the spring set 15, each of the grooves 14c, 14d forms a through-hole. Alternatively, components 14 and 15 could be formed as an integral unit.

Figure 9A:
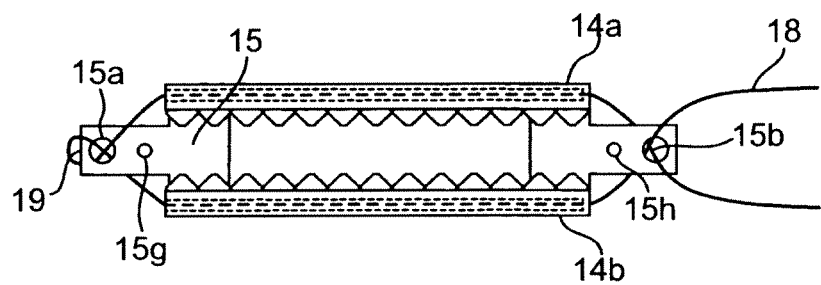

After the jaws 14a, 14b are attached to the spring set 15, a jaw operating cable 18 is connected to the jaw assembly 14. As shown in FIG. 9A, one end of the jaw operating cable 18 passes, in order: (a) through a proximal opening 15b of the spring set 15; (b) through the through-hole formed by one of the grooves 14c, 14d and one arm 15c, 15d of the spring set 15; (c) through the distal opening 15a of the spring set 15; (d) through the through-hole formed by the other groove 14c, 14c and the other arm 15c, 15d of the spring set 15; and (e) again through the proximal opening 15b of the spring set 15. When the cable 18 passes through the distal opening 15a, the operating cable 18 is, preferably, twisted to form a small loop 19, as shown in FIG. 9A. By forming this loop 19, an inwardly directed force F exerted when the cable 18 is pulled is more uniformly distributed along the side length of the cable 18, as shown in FIG. 9B.

Figure 9B:
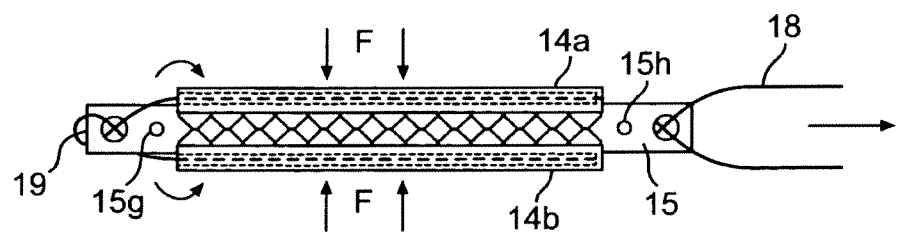
Figure 10:
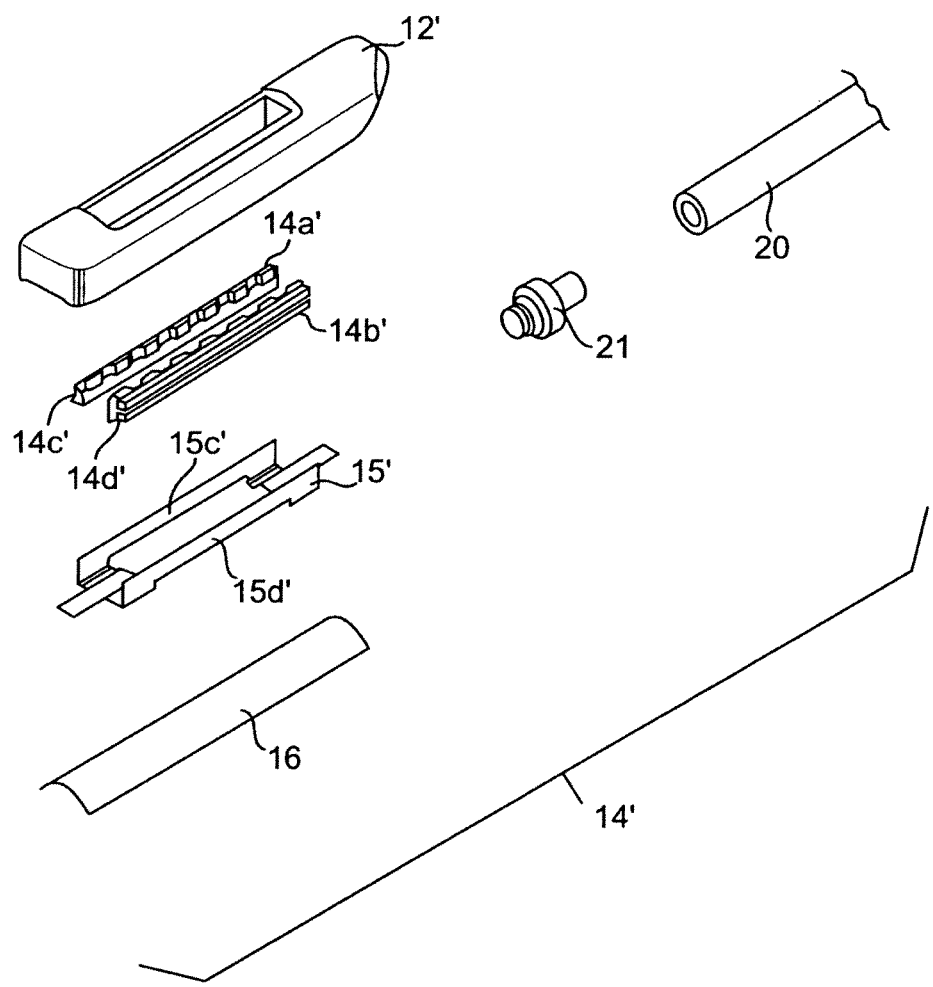
FIG. 10 is a perspective view showing various components of an invagination head, according to another embodiment of the present invention.
Figure 11A:
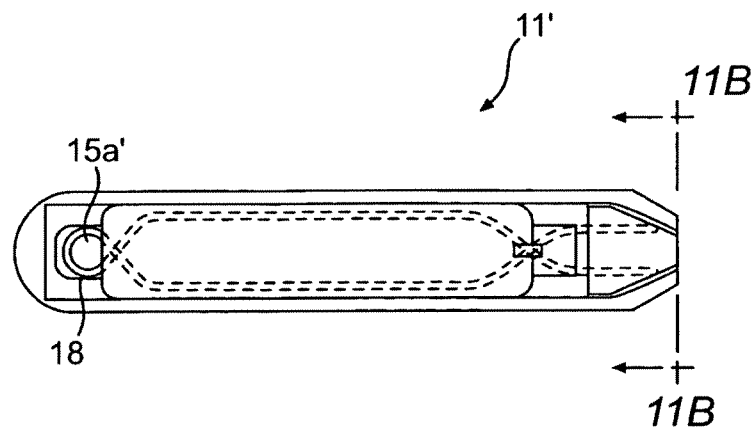
FIGS. 11A and 11B are bottom and side views, respectively, of the invagination head shown in FIG. 10 in the assembled state.
Figure 11B:
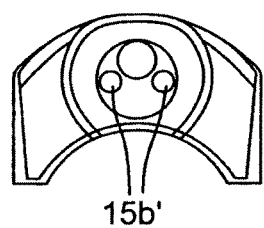

FIGS. 10, 11A, and 11B show an alternative embodiment of an invagination head. As shown in FIG. 10, spring set 15' may have a U-shaped configuration in the unbiased state with its side arms 15c', 15d' projecting substantially perpendicular to the planar surface of the spring set 15'. Each jaw 14a', 14b' having a groove 14c', 14d' or through-hole for accommodating cable 18 may be welded or otherwise affixed to each side arm 15c', 15d'. In this embodiment, as shown in FIG. 11A, cable 18 may be wrapped around a distal post 15a' at the distal end of the main body 12', rather than using openings 15a and 15*b* shown in FIGS. 8A, 9A, and 9B. For example, cable 18 may pass, in order: (a) through the through-hole formed by one of the grooves 14*c*', 14*d*' and one arm 15*c*', 15*d*' of the spring set 15'; (b) around the distal post 15*a*'; and (c) through the through-hole formed by the other groove 14*c*', 14*d*' and the other arm 15*c*', 15*d*' of the spring set 15'. By wrapping the cable 18 around the post 15*a*', an inwardly directed force F exerted when the cable 18 is pulled also is more uniformly distributed along the side length of the cable 18. In an embodiment, the proximal end portion of the main body 12' may include openings 15*b*' for receiving cable 18 extending thereto, as shown in FIG. 11B.

Other alternative wrapping configurations and methods may be used wherein cable 18 is guided through alternative looping, knotting, or tying patterns, and components 14 and/or 15 have other openings than those shown in the Figures and described above. As a further alternative, cable 18 may be welded or otherwise affixed to tabs 15*e*, 15*f* of spring set 15, without the need for holes 15*a*, 15*b* or grooves 14*c*, 14*d*.

In operation, pulling the jaw operating cable 18 in a proximal direction (by an actuation handle further described herein) causes the flexible spring set 15, 15' to deform into a folded configuration, causing the pair of jaws 14*a*, 14*b*, 14*a*', 14*b*' to move towards each other, as shown in, for example, FIG. 9B. The spring set 15, 15' is preferably made of a flexible, elastic material, such that the jaws 14*a*, 14*b*, 14*a*', 14*b*' can remain in a biased-open state when the operating cable 18 is released.

Once the jaw assembly 14, 14' is properly connected to the jaw operating cable 18, the jaw assembly 14, 14' can be attached to the main body 12, 12' by a suitable fixing mechanism, such as, for example, screws or welding. In the embodiment shown in FIG. 8A, each of the side tabs 15*e*, 15*f* includes a screw opening 15*g*, 15*h* for fixedly attaching the jaw assembly 14 to the main body 12. After the jaw assembly 14, 14' is attached to the main body 12, 12', the concave insert 16 is attached to the main body 12, 12' to cover the back side of the main body 12, 12'. The main body 12, 12' and the concave insert 16 then forms a hollow space therebetween to which a suitable vacuum is to be applied.

The invagination head 11 is connected to a distal end of the elongated conduit 20 via a suitable connecting member 21, such as, for example, a threaded bolt-nut arrangement, a snap-fit, a bond, a weld, as an integral component, or via any suitable means known in the art. The conduit 20 can be a hollow, single or multiple wound coil 20 covered with a suitable heat shrink material. Conduit 20 may comprise any of the conduit forming means known in the art, including, for example, a solid polymer tube, tubes having reinforcing braids, coils, weaves, or fibers, layered tubes, variable stiffness tubes, or the like. The conduit 20 may include more than one lumen. For example, while a single lumen of the conduit 20 can accommodate both the vacuum suction path and the jaw operating cable 18, the conduit 20 may be provided with separate lumens for accommodating them separately. The conduit 20 is sufficiently flexible to traverse tortuous anatomy of a body, yet rigid and strong enough to move the grasped esophageal tissue down toward the stomach during, for example, a fundoplication procedure. Other suitable conduits having similar characteristics can be utilized instead.

Figure 12:
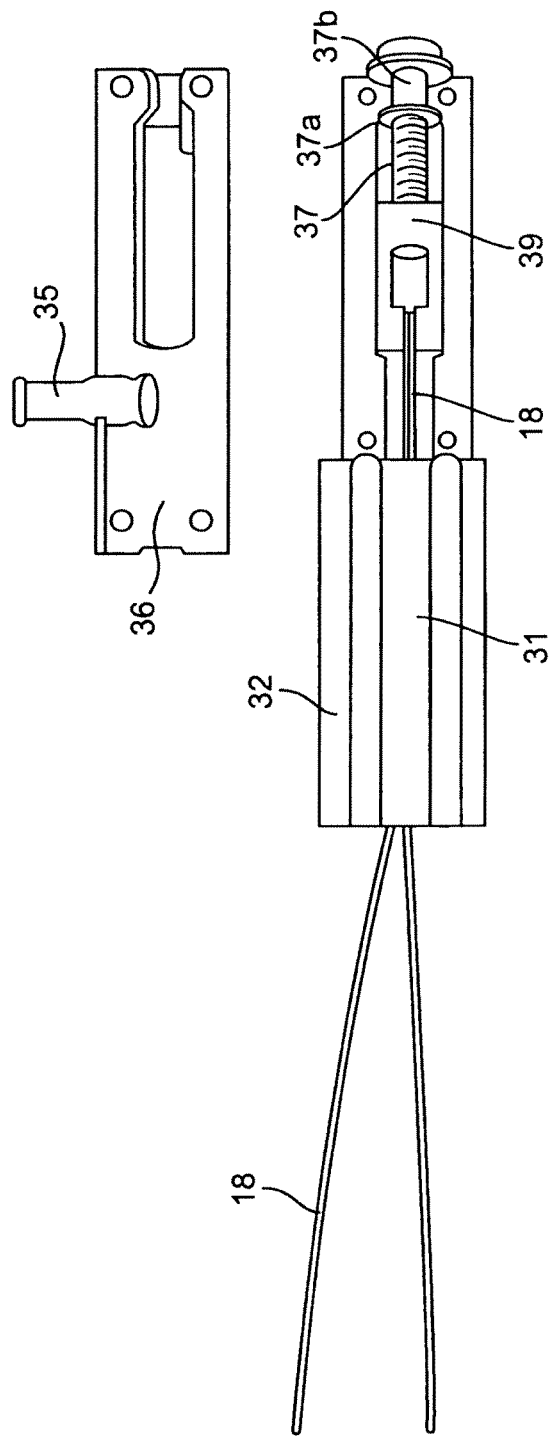
FIG. 12 is a perspective view of an invagination handle, showing its major components, according to an embodiment of the present invention.
Figure 13:
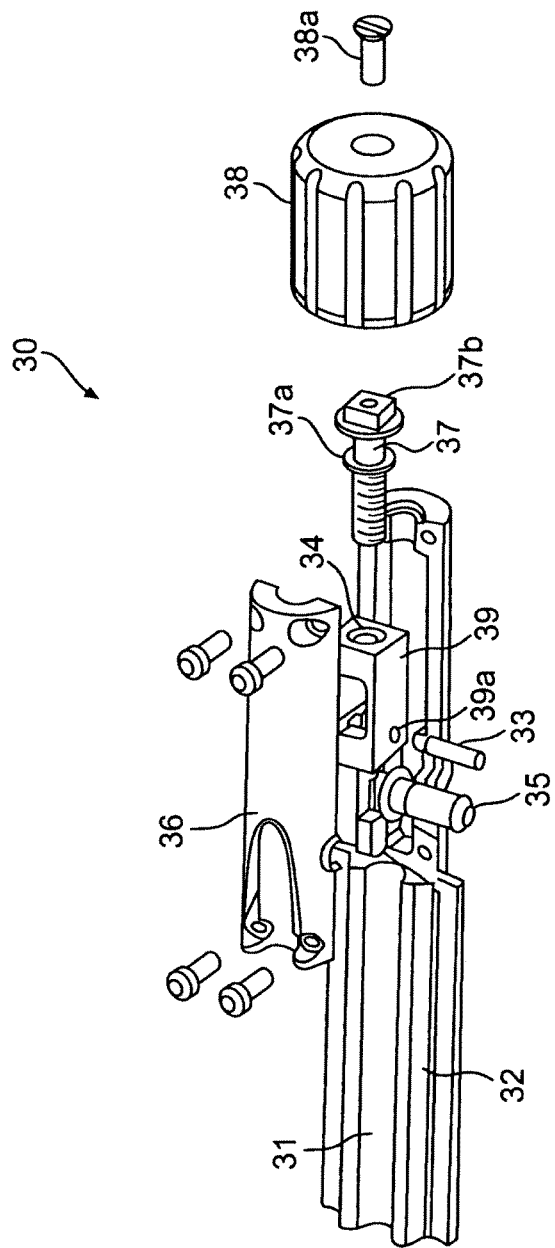
FIG. 13 is an exploded perspective view of the invagination handle shown in FIG. 12, showing various components of the invagination handle.

At its proximal end, the conduit 20 connects to a suitable actuation handle. FIGS. 12 and 13 show an actuation handle 30 used for operating the invagination head 11 including the jaw assembly 14, according to an embodiment of the present invention. The handle 30 includes a base 32, a cover 36, and a jaw knob 38. The base 32 has a hollow bore 31 in fluid communication with a lumen of the elongated conduit 20. The cover 36 has a tube fitting 35 to which a source of vacuum (not shown) can be connected. To seal off the fluid path from the tube fitting 35 to the invagination head 11, various sealing members, such as, for example, O-rings, rubber seals, etc., can be used throughout the device 10. When the source of vacuum connected to the tube fitting 35 is turned on, it creates a suction force in the opening 13 of the invagination head 11, sucking and holding the tissue in the vicinity of the opening 13. The actuation handle may be made as an integral unit or separate parts that may be snap fit or otherwise affixed to one another so as to keep a fluid tight suction path.

The lines of the operating cable 18 pass through the bore 31 of the base 32 to a section of the base 32 covered by the cover 36. These lines of the cable 18 are crimped together and positioned around a pin 33. The pin 33 extends through and connects with a follower 39 inside the base 32. The follower 39 includes holes 39*a* to receive the pin 33 and a threaded hole 34 into which a threaded shaft 37 is inserted, such that the follower 39 can move axially along the threaded shaft 37. The threaded shaft 37 is disposed inside the proximal portion of the base 32 with its head 37*b* protruding out of the base 32. While the axial movement of the threaded shaft 37 is limited by a flange 37*a* or a washer, the threaded shaft 37 is freely rotatable relative to the base 32 to move the follower 39 along the threaded shaft 37. Rotation of the threaded shaft 37 causes the follower 39 to move axially along the threaded shaft 37, which in turn pulls or pushes the operating cable 18 for opening and closing the jaws 14*a*, 14*b*, depending on the direction of rotation of the shaft 37. The protruded head 37*b* of the shaft 37 is then mechanically coupled to the jaw knob 38 to facilitate rotating of the threaded shaft 37. This coupling may be achieved by a screw 38*a* extending through the knob 38 and into the head 37*b*, or any other suitable coupling.

For operation of the invagination device 10, a source of vacuum is connected to the tube fitting 35 to create a desired level of suction in the invagination head 11. The vacuum in the head 11 causes the tissue in the vicinity of the opening 13 of the head 11 to be sucked into and held in the opening 13. Once the tissue is properly held in the opening 13, the jaw knob 38 is rotated in the proper direction to cause axial movement of the follower 39 in the proximal direction away from the invagination head 11. The movement of the follower 39 then pulls the operating cables 18 and causes the pair of jaws 14*a*, 14*b* to close and grasp the tissue held in the opening 13 by suction. Suction can be continued, if desired, or tissue can be grasped by the force of the jaws 14*a*, 14*b* alone.

In alternative embodiments, various other types of tissue holding/grasping means, such as, but not limited to, needles, clamps, forceps, balloons, hooks, and suction cups or tubes, can be utilized. FIGS. 14-29 show the distal ends of various alternative embodiments of invagination devices, according to the invention, as described further herein. That distal ends connect to any suitable elongated conduits, or catheters, that are configured to extend from outside the patient, through the esophagus, and to the LES. The distal ends of the various invagination devices shown may be operated by any suitable actuation handles positioned at the proximal end of the elongated conduit, including actuation handles similar to that used in the embodiment of FIGS. 4-13.

Figure 15:
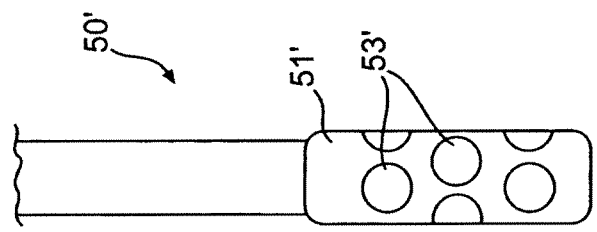
Figure 14:
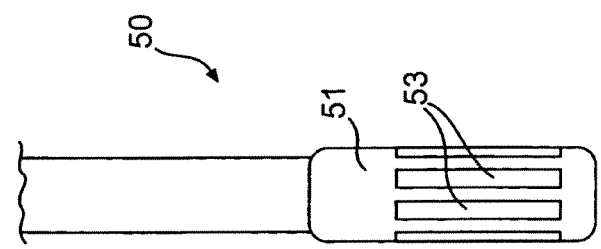

FIG. 14 shows the distal end of an invagination device 50 utilizing a suction mechanism, similar to the embodiment shown in FIGS. 4-13, according to another embodiment of the present invention. In this embodiment, however, a head 51 forms a generally cylindrical tube having a plurality of suction openings 53. While the plurality of openings 53 are shown to have uniform openings 53 throughout the circumference of the tubular head 51 with a substantially equal distance between the openings 53, the head 51 may also have non-uniform arrangements of the openings 53. For example, a certain portion of the head 51 may not form any openings 53 at all. The number, shape, and size of the openings 53 may also vary depending on the type of surgical procedures and their needs, such as, for example, type of tissue to be held, firmness of the holding, etc. In an alternative embodiment, a head 51' has a plurality of circular openings 53', as shown in FIG. 15.

Figure 16:
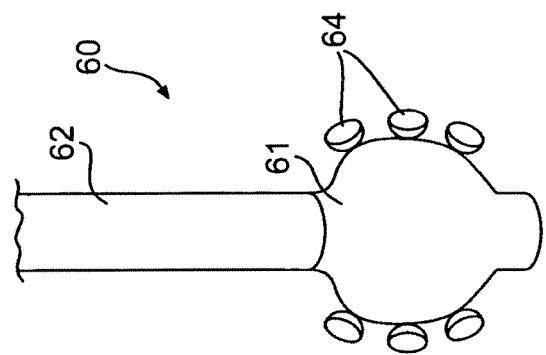

FIG. 16 shows the distal end of an invagination device 60 utilizing a plurality of suction cups 64 for holding the tissue to be invaginated, according to still another embodiment of the present invention. Similar to the embodiment shown in FIGS. 4-13, a vacuum source is supplied to each of the suction cups 64 through a conduit 62. Preferably, an inflatable balloon 61 is positioned at a distal end of the conduit 62 so that when the vacuum suction is activated, the balloon 61 can be inflated to bring the suction cups 64 in contact with the tissue to be invaginated, as shown in FIG. 16. Inflation of balloon 61 may be achieved by connection to a source of air or any other fluid via an inflation lumen in the conduit 62. Once the tissue is securely held by the plurality of suction cups 64, the balloon 61 can be deflated to reduce the cross-sectional area of the distal end of the device 60. The invagination device 60 holding the tissue to be invaginated is then advanced toward the stomach to move and invaginate the tissue. Although FIG. 16 shows two sets of three suction cups 64, there may be any number, size, arrangement, or pattern of cups 64 to achieve the desired purpose of holding tissue. In addition, cups 64 may be used to cover grasping means, such hooks, barbs, or anchors, attached to balloon 61. When balloon 61 is inflated, the grasping means may be exposed to grasp tissue, and when balloon 61 is not inflated, the grasping means may be unexposed.

Figure 17:
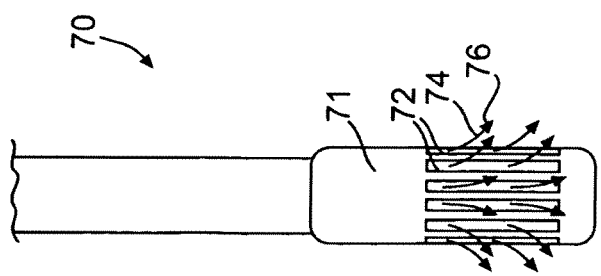

In another embodiment of the present invention, FIG. 17 shows the distal end of an invagination device 70 having a plurality of needles 74 for holding tissue to be invaginated. In this embodiment, the invagination head 71 is a generally cylindrical tube having a plurality of openings 72 through which the plurality of the needles 74 extend radially toward the tissue to be invaginated. Each of the needles 74 may include a barbed distal end 76 to pierce through and hold the tissue. Alternatively, needles 74 may not include barbed ends, which will promote easier removal of needles 74 from tissue after needles 74 help promote invagination.

The needles 74 are configured to remain in a retracted position inside the head 71 during delivery of the device 70. Once the head 71 is placed proximate to the tissue to be invaginated, the plurality of needles 74 are guided to extend in radial direction and pierce the tissue to be invaginated. The needles 74 are flexible, yet sufficiently rigid to pierce through the tissue. The needles 74 with barbed ends 76 can push and drag the tissue downward when the invagination device 70 is displaced downwardly toward the stomach. The size and shape of the barbed distal ends 76 may be selected to minimize trauma to the patient, but at the same time, to sufficiently hold the tissue during the invagination procedure. The size, shape, and number of openings 72 may vary.

A further embodiment includes a barb activation means to deploy or retract barbs at the distal end of the needles. As an example, barbs may be within hollow needles and pushed forward or retracted relative to the needle, as desired. As a further alternative, barbs may be compliant so as to grasp and lift tissue but have sufficient flexibility to be removed from the tissue if sufficient force is applied. The barbs also may have a slightly rounded or ball-like shape to assist in removing the barbs from tissue. As an even further embodiment, the needles may be paired so as to lock together after piercing tissue and released through application of force for removal from tissue.

Figure 18:
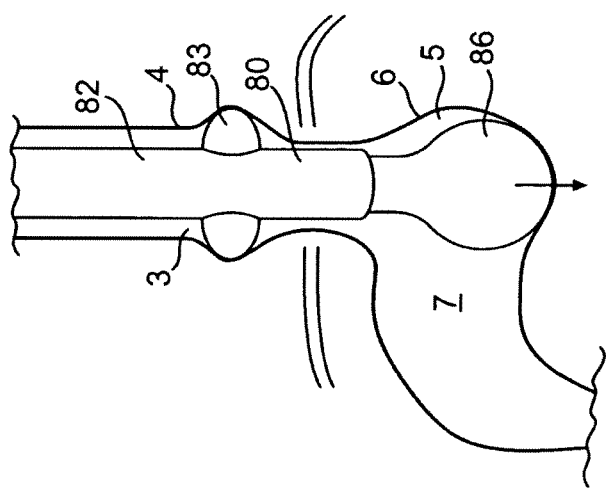

FIG. 18 shows another embodiment of an invagination device 80 positioned within esophagus 3 and stomach 7. The device 80 has an expandable distal member 86 to stretch the esophageal tissue or hiatal hernia tissue toward the stomach. The distal member 86 may be a balloon, a rod, or any other suitable structure configured to extend in the distal direction. The distal member 86 preferably moves axially within the main body 82 of the device 80. As shown in the figure, the distal member 86 is advanced into the stomach and expands its distal portion to push the fundus wall 6, causing the esophageal tissue 4 or the hiatal hernia tissue to stretch into the stomach 7. Expansion of the distal member 86 may be achieved by inflation of the distal portion of the member 86, self-expansion as the member 86 extends from the body 82, or any other suitable method. The main body 82 of the device 80 may include a holding member 83, such as, for example, a balloon, a clamp, suction, anchors, or the like to hold an upper portion of the esophagus wall 4 while the distal member 86 pushes the fundus wall 6 to stretch the esophagus wall 4.

Figure 19:
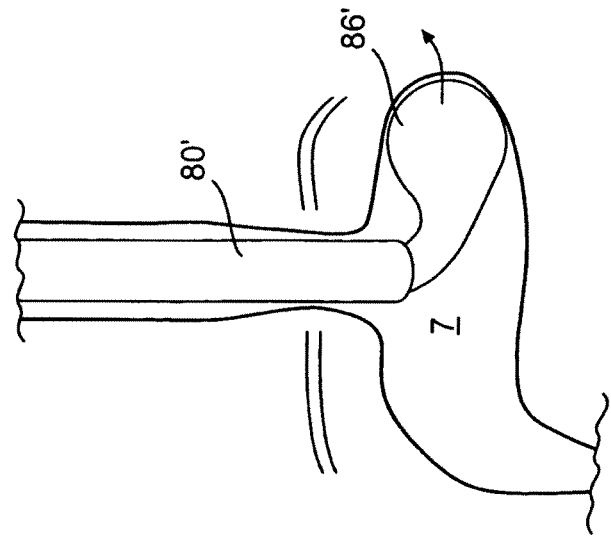

FIG. 19 shows an embodiment similar to that of FIG. 18, without a holding member 83. As shown in FIG. 19, an expandable member 86', such as a balloon, may also be configured to lift and stretch the fundus 5 to fold the stomach wall 6 to the esophagus. Likewise, member 86 of FIG. 18 may be used to fold stomach wall 6. To do so, each of members 86, 86' may be shaped in a bent manner and lift as it is inflated, configured so that one of its sides inflates and grows prior to other sides during inflation, or otherwise configured to fold stomach 6 during inflation. Alternatively, a device or tool placed within or otherwise adjacent member 86, 86' may be used to push or pull up one side of member 86, 86'.

Figure 20:
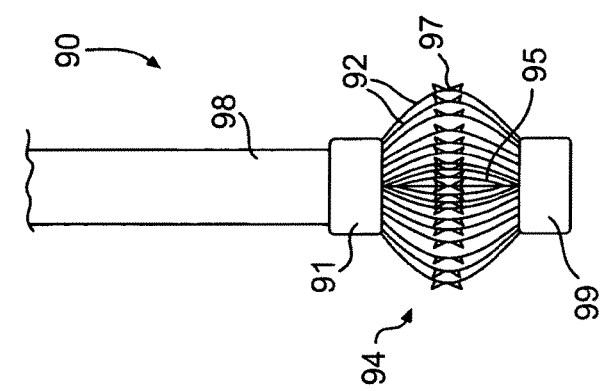

FIG. 20 shows the distal end of an exemplary invagination device 90 utilizing an interference-fit mechanism, according to another embodiment of the present invention. The invagination device 90 includes a radially expandable member 94 having friction/grasping members 97 disposed on at least a portion of the expendable member 94. In this embodiment, the expandable member 94 includes a distal portion 99 and a proximal portion 91, interconnected by an actuation rod 95 and a plurality of flexible wires 92. Each of the wires 92 includes a member 97, such as, for example, a hook or pointed projection.

Preferably, the distal end of the actuation rod 95 is fixedly connected to the distal portion 99 while the proximal end of the actuation rod 95 is movably connected to the proximal portion 91, such that the distal and proximal portions 99, 91 are axially moveable relative to each other. The actuation rod 95 is flexible, yet rigid enough to move the distal portion 99 without bending. The plurality of wires 92 are made less rigid than the actuation rod 95 and, preferably, formed of a flexible, elastic material. During deployment, the distal and proximal portions 99, 91 of the expandable member 94 are separated apart by the length of the wires 92, so that the wires 92 form a substantially straight outer profile. Once the expandable member 94 is positioned proximate to the tissue to be invaginated, the distal and proximal portions 99, 91 are moved toward each other by pulling the actuation rod 95 in the proximal direction. This movement causes the plurality of wires 92 to bend outwardly and bring the members 97 in contact with the tissue to be invaginated. At this point, the tissue holding force applied by the members 97 through friction, grasping, snagging, or the like, is sufficient enough to maintain the firm holding while the device 90 is pushed down toward the stomach for invagination. It should be understood that any other suitable activation mechanisms for expanding the plurality of wires 92 can be employed instead.

As an alternative embodiment, wires 92 may include a portion with a temporary adhesive or having a friction promoting surface, such as by addition of a suitable coating or otherwise shaping or scoring the surface, for adhering to tissue. Such an adhesive or friction promoting surface may be used in other embodiments described herein.

As an alternative, the wires 92 may be fixedly connected to the distal portion 99, but slidable within proximal portion 91. In this case, when the invagination device 90 is inserted into the esophagus, the actuation rod 95 may be pulled in the proximal direction so that the distal and proximal portions 99, 91 contact each other and the wires 92 are contained within the proximal portion 91 and its connected elongated conduit 98. In this manner, a risk of tissue damage to the esophagus during insertion can be minimized. When the device 90 is at the desired position in the esophagus, the actuation rod 95 may be extended in the distal direction to separate the distal and proximal portions 91, 99 and expose the wires 92 and the friction members 97 to hold the esophageal tissue. As a further alternative of the embodiment shown in FIG. 20, the proximal and distal portions 91, 99 and the expandable member 94 may have a smaller profile (cross sectional dimension) than the elongated conduit 98 of the device 90 to minimize tissue trauma during insertion.

Figure 21:
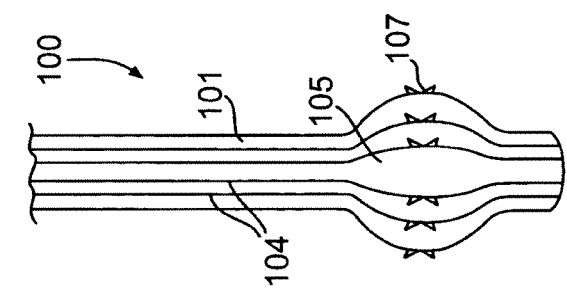

In an alternative embodiment shown in FIG. 21, an invagination device 100 may include a flexible, expandable tube 101 having an expandable portion 105 having friction members 107 disposed on at least a portion of its outer surface. The expandable tube 101 may be reinforced with a plurality of flexible wires 104.

Figure 22:
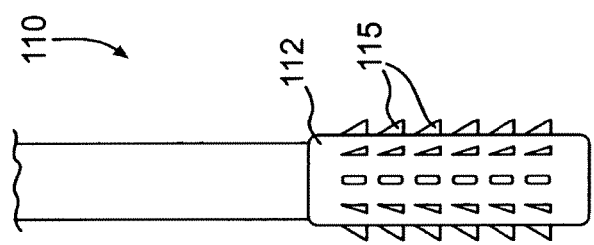

FIG. 22 shows the distal end of an invagination device 110 having a plurality of projections 115 on an invagination head 112, according to still another embodiment of the present invention. Similar to the embodiment shown in FIG. 21, the device 110 utilizes an interference-fit mechanism to hold the tissue to be invaginated. After the invagination head 112 is advanced into the esophagus 3, the head 112 is brought in contact with the tissue to be invaginated. The head 112 may be configured to expand radially, so that the outer surface of the head 112 contacts the tissue to be invaginated when expanded. The friction/grasping force between the plurality of projections 115 and the tissue is sufficient enough to hold the esophageal tissue while the device 110 is pushed down toward the stomach for invagination.

The embodiment shown in FIG. 22 or any other suitable embodiment described herein may be used in a retrograde fundoplication procedure. In such a procedure, the esophagus is first tightened by pulling it upwards to straighten a hiatal hernia. This may be accomplished with any suitable mechanism known in the art, such as an endoscopic or trans-esophageal device employing suction, graspers, hooks, or the like. While the esophagus is being help up, an invagination device, such as those described herein, may be used below the help up portion of the esophagus to push the esophagus downward to prepare for fundoplication and correct the herniated stomach.

Figure 23:
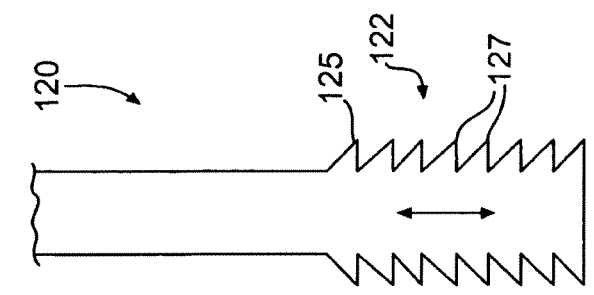

FIG. 23 shows the distal end of an invagination device 120 having a bellow-like invagination head 122, according to still another embodiment of the present invention. The invagination head 122 is preferably configured to extend and contract in the axial direction. During deployment, the head 122 extends axially to form a substantially smooth outer profile. Once the head 122 is positioned proximate to the tissue to be invaginated, the head 122 contracts axially, causing traction fins 127 of the bellow-like head 122 to radially extend and contact the tissue, as shown in FIG. 23. The extended traction fins 127 provide sufficient friction force to firmly hold the esophageal tissue while displacing the invagination device 120 down toward the stomach. The traction fins 127 can have a variety of shapes and sizes.

FIG. 24 shows the distal end of another embodiment of an invagination device 130 having an invagination head 132 formed of inter-linked wires 133 in an umbrella-like configuration. The proximal ends of the wires 133 join at a central member 131. Umbrella-like struts (not shown) may interconnect wires 133 within the interior of head 132. The operation of the head 132 can be fundamentally the same as that of an umbrella. For example, the device 130 may include an actuation member (not shown) located in the central axis of the arrangement of the wires 133, and the mid-portion 135 of each wire 133 is connected to the distal end portion of the actuation member through the umbrella-like struts. The actuation member is axially movable with respect to the central member 131 to which the proximal ends of the wires 133 are connected. During insertion of the device 130 into the esophagus, the actuation member is pulled proximally, which in turn causes the wires 133 to collapse into a smaller cross-sectional area. Once the head 132 is positioned proximate to the tissue to be invaginated, the actuation member is extended distally, causing the wires 133 to expand radially outwardly to contact the tissue, as shown in FIG. 24. Other suitable mechanisms for deploying the wires 133 may be used. The outer surface of the head 132 formed by the wires 133 may include an additional frictional member (not shown), such as hooks or pointed projections, or a coating or covering, to enhance the holding force between the head 132 and the tissue. The extended wires 133, together with the friction members, provide sufficient friction force to firmly hold the esophageal tissue while displacing the invagination device 130 down toward the stomach for invagination. Expansion of head 132 alternatively may be caused by a balloon or other dilating member.

As a further alternative, head 132 may operate like a partial exposed, self-expanding stent. In this embodiment, head 132 is not connected to member 131 and instead slides within and relative to the outer tube. As head 132 exits the distal end of the tube, it naturally self-expands to contact the esophagus. As another embodiment, head 132 may be configured to bend backwards on itself to create a flange-like head at its end that would contact the esophagus. The head may be coated or covered to have a friction surface to assist in invagination. Head 132 may also include hooks, barbs, or other graspers therein that may be exposed between wires 133. As an even further alternative, head 132 may operate like an expandable stent, which may be expanded by a balloon or other suitable dilating mechanism.

FIG. 25 shows the distal end of an invagination device 140 formed of an expandable tubular body 145, such as, for example, a stent, according to still another embodiment of the present invention. The tubular body 145 may be a self-expandable body or expandable by means such as a balloon, a dilator, an expandable cage, or the like. Body 145 has tapered distal and proximal end portions 149, 141. The tubular body 145 may be formed by braiding or knitting a plurality of flexible wires 147 or filaments to provide sufficient radial expansion force. The wires 147 can be made of metal, polymer, composites thereof, or other suitable materials known in the art, which exhibit sufficient elasticity, such as a memory material like nickel titanium alloy (i.e., nitinol). During deployment, the tubular body 145 is contracted into a smaller cross-sectional area by using a suitable deployment device, such as a sheath covering the contracted body 145, to permit easy passage through the esophagus. Once the tubular body 145 is positioned proximate to the tissue to be invaginated, the tubular body 145 is released to self-expand radially to contact the tissue to be invaginated, as shown in FIG. 25. At least a portion of the outer surface of the tubular body 145 may include a friction member, such as hooks, barb-like projections, a covering, a coating, or the like to enhance grasping force between the tubular body 145 and the tissue. The tubular body 145, together with the friction member, provides sufficient friction force to firmly hold the esophageal tissue while displacing the invagination device 140 down toward the stomach for invagination. In further embodiments, end portion 149 may be shaped to enhance contact with the esophagus. Such embodiments may include a flared end or a "T" shaped end, or other shaped end of increased diameter relative to body 145.

FIG. 26 shows the distal end of an invagination device 150 having a plurality of rotating members, such as wheels 155, to displace the esophageal tissue down toward the stomach, according to still another embodiment of the present invention. As shown in the figure, each of the wheels 155 has a rotating axis 157 disposed in the invagination head 152 with a portion of the wheel 155 protruding beyond the outer profile of the head 152. The device 150 includes suitable means for driving the wheels 155, such as, for example, a driving belt or rod 156. Once the invagination head 152 is properly positioned proximate to the tissue to be invaginated, the means for driving the wheels 155 is activated to rotate the wheels 155 in the direction shown by the arrows in the figure. With the invagination head 152 fixed stationary in a position, the rotating wheels 155 hold the tissue and displace the tissue down toward the stomach for invagination. Rotating members, such as wheels 155, may have any suitable outer surface, either smooth or roughened, barbed, covered, coated, etc. as desired to appropriately hold and move the tissue. In addition, any number or configuration of rotating members may be used, as desired.

FIG. 27 shows the distal end of an invagination device 160 having an invagination head formed of a T-shaped configuration, according to still another embodiment of the present invention. The device 160 includes a main body 161 and a rotating body 165 rotatable with respect to a pivoting member 168 of the main body 161. The rotating body 165 preferably includes a pointed edge 167 on at least one end of the body 165 for piercing the tissue to be invaginated. The device 160 also includes an actuation member 163, such as, for example, a cable or rod, for rotating operation of the rotating body 165. The actuation member 163 is relatively flexible, yet rigid enough to pull and push the rotatable body 165 without bending. Preferably, one end of the actuation member 163 is fixedly connected to the rotatable body 165 while the other end of the actuation member 163 is slidably coupled to the main body 161. This connection arrangement of the actuation member 163 allows pivotal movement of the rotatable body 165 with respect to the main body 161 to form a T-shaped invagination device 160. During insertion into the esophagus, the actuation member 163 is pulled proximally to align the rotatable body 165 substantially parallel to the main body 161 in order to permit easy passage through the esophagus 3. Once the invagination device 160 is properly positioned proximate to the tissue to be invaginated, the actuation member 163 is pushed distally to pivotally rotate the rotatable body 165 approximately 90°, or any other desired angle, with respect to the main body 161 to form a T-shaped configuration. The pointed edge 167 may then pierce the tissue to be invaginated and firmly hold the tissue. The pointed edge 167 of the rotatable member 165 sufficiently holds the tissue while the invagination device 160 is displaced down toward the stomach for invagination. In a further embodiment, distal end of device 160 may have a sheath, sac, cage, or other like structure covering the "T". When the "T" is actuated, it would expand that structure, which would cause the structure to contact the esophagus. The structure may be coated or otherwise configured to enhance its holding force against the esophagus.

Figure 28:
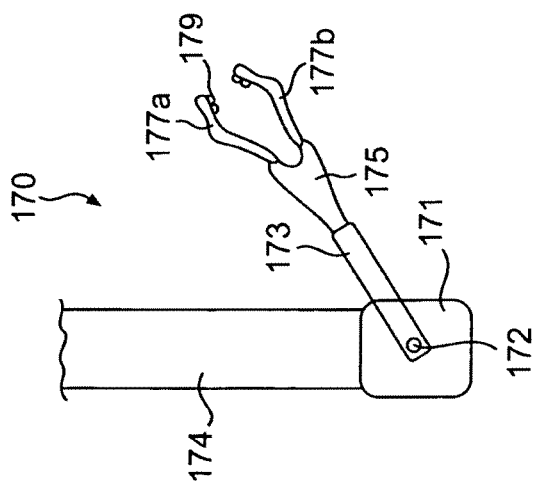

FIG. 28 shows the distal end of an invagination device 170 having a rotatable arm 173 with means for grasping a tissue to be invaginated, according to still another embodiment of the present invention. In this embodiment, a rotatable arm 173 is rotatably coupled to a pivot member 172 disposed in the distal portion 171 of the conduit 174. At its distal end, the arm 173 includes a pair of grasping jaws 177a, 177b or forceps having a plurality of teeth 179. The rotatable arm 173 has an intermediate bushing member 175 to guide the pair of jaws 177a, 177b in and out of the rotatable arm 173 to open and close the jaws 177a, 177b. The jaws 177a, 177b may be configured to open when moved out of the bushing member 175 and to close when retracted into the rotatable arm 173. The jaws 177a, 177b may be spring-loaded or otherwise activated through pull wires or other suitable actuation device known in the art (not shown) to pull or release the jaws 177a, 177b. During operation, when the device 170 is properly positioned proximate to the tissue to be invaginated, the rotatable arm 173 is rotated to face the pair of jaws 177a, 177b toward the tissue to be invaginated. Articulation/rotation of arm 173 may be achieved by use of pull wires or pre-curved portions of the device. In addition, the pull wire(s) may be activated by using a shape memory material (such as metal or plastic), by applying heat or electricity to induce pulling and cause articulation, or by any other suitable activation method known in the art. After articulation, jaws 177a, 177b may be closed to hold the tissue. While holding the tissue, the device 170 can be displaced down toward the stomach. As alternatives, any other suitable jaws or forceps known in the art can be utilized. The device 170, including the jaws 177a, 177b, may also include heat transfer capabilities for various purposes known in the art.

As further embodiments of the invention, any of the embodiments of invagination devices described herein may be configured to articulate so that the grasper, suction device, or other mechanism to grasp or otherwise hold tissue may be placed proximate the esophagus.

Figure 29:
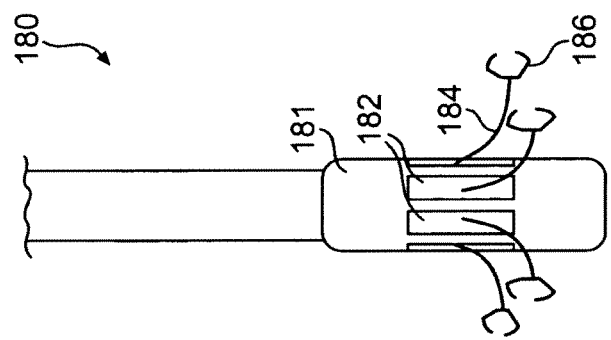

FIG. 29 shows the distal end of an invagination device 180 having a plurality of wires 184 each having a grasper 186, such as jaws or forceps, on its distal end, according to still another embodiment of the present invention. This embodiment is similar to the embodiment shown in FIG. 17, except that each of the needles 74 in FIG. 17 is replaced with a wire having the grasper 186. Each of the wires 184 extends radially out of an opening in the device head 181 toward the tissue to be invaginated. Each of the wires 184 includes actuation means (not shown) for opening and closing the graspers 186. The actuation means may include an activation wire extending through and slidably within the wire 184, if the wire 184 were in the form of a tube. Once the head 181 is placed proximate to the tissue to be invaginated, the plurality of wires 184 extend radially toward the tissue to be invaginated. The actuation means in the wires 184 is then activated to close the graspers 186 to grasp the tissue. The size and shape of the graspers 186 may vary depending on the type of tissue to be invaginated and the type of surgical operation. Other operational characteristic of the invagination device 180 is similar to the embodiment shown in FIG. 17.

FIG. 30 shows an exemplary A-frame device 200 used in, for example, a fundoplication procedure, according to an embodiment of the present invention. The various exemplary invagination devices disclosed herein may be used in connection with an A-frame device, such as the one shown in FIG. 30. The A-frame device 200 includes an A-frame head 220, an A-frame handle 280, and a downtube 250.

Figure 31A:
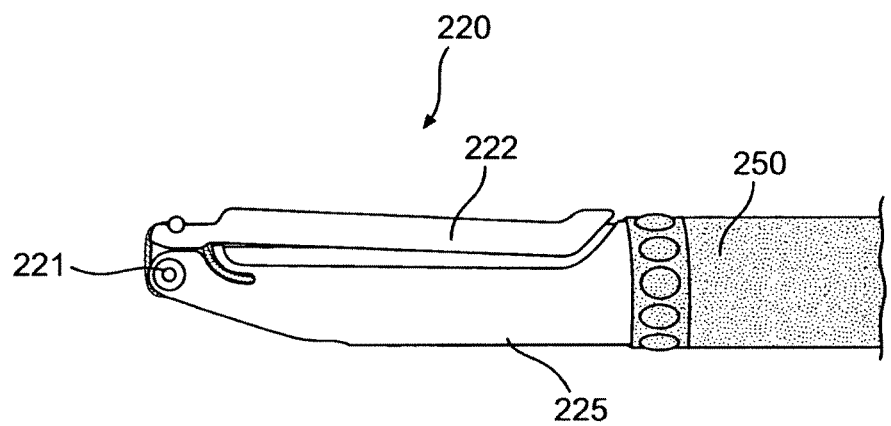
FIGS. 31A-31B are side and top views of an A-frame head, respectively, with a folding arm in a closed position, according to an embodiment of the present invention.
Figure 31B:
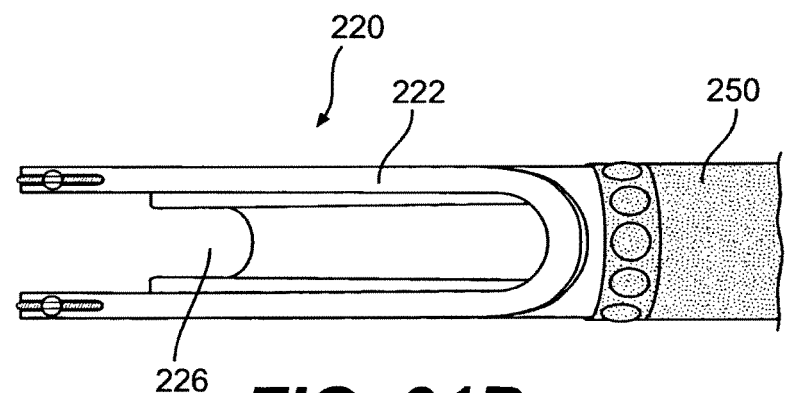

The A-frame head 220, shown in more detailed in FIGS. 31A-31C, is a relatively short cylindrical tube having a main body 225 and a folding arm 222. The proximal end of the folding arm 222 (i.e., the end-most proximal part when the arm 222 is in the open position) is rotatably coupled to a pivot member 221 disposed in the distal end portion of the main body 225. The outer profile of the folding arm 222 is preferably configured such that, in the closed position, shown in FIGS. 31A and 31B, the folding arm 222 is substantially flush with an outer surface of the main body 225, and forms a generally cylindrical outer profile with the main body 225. In the open position, as show in FIG. 31C, the folding arm 222 rotatably extends to receive tissue layers to be folded between the folding arm 222 and the main body 225. The folding arm 222 has a generally U-shaped configuration defining an opening 226 or a slot along its length to permit passage of fastening devices and fastening members after the tissue layers are folded together and ready to be fastened. On the inner surface of the folding arm 222, a friction-enhancing member 228, such as, for example, a plurality of teeth, are formed to tightly hold the tissue layers during the folding and holding operations. In addition, at least a portion of the A-frame head 220 may be coated with a polymer or elastomer material, or any other friction enhancing material known in the art (including ceramics and metals), to provide a softer contact between the tissue and the A-frame head 220 and/or to enhance the grip of the A-frame head 220 on the tissue.

The downtube 250 connects to the A-frame head 220 and the A-frame handle 280 at its distal and proximal ends, respectively. The downtube 250 can extend from outside of a body to a site deep within the body, and is sufficiently flexible to traverse through tortuous paths within a body, such as, for example, to the gastroesophageal junction site. The downtube 250 contains a plurality of lumens that are designed to encompass various operating devices, such as, for example, endoscopes and invagination devices, and related activation means, such as, for example, cables and rods, for manipulating the operating devices.

Preferably, the various invagination devices disclosed herein are configured to be slidably insertable through a lumen of the A-frame device 200. For example, an invagination device has an outer diameter slightly less than the inner diameter of a working channel of the A-frame device 200, so that the invagination device can axially move within the working channel of the A-frame device 200.

It should be understood that, in place of the A-frame device 200 shown in FIGS. 30 and 31A-C, the invagination devices disclosed herein can be used with any other conventionally known endoluminal surgical devices, such as those described in U.S. Pat. No. 6,086,600, the disclosure of which is hereby incorporated by reference. As an alternative, at least some of the embodiments disclosed herein can be built into and made integral with an A-frame device or any other surgical device known in the art.

While the exemplary embodiments disclosed herein are described in connection with endoluminal procedure, it should be recognized that some of the embodiments may be utilized in various laproscopic procedures. That is, the disclosed invagination devices may be introduced through a small incision into the stomach to pull the interior of the esophagus 3 into the stomach 7.

With reference to FIGS. 32 through 38, an exemplary method of invaginating the esophageal tissue toward the stomach, according to an embodiment of the present invention, is described herein. For the purpose of a comprehensive illustration, the invagination device shown in FIGS. 4 and 5, in connection with the A-frame device 200 shown in FIG. 30, is used to describe the method of invagination.

Figure 32:
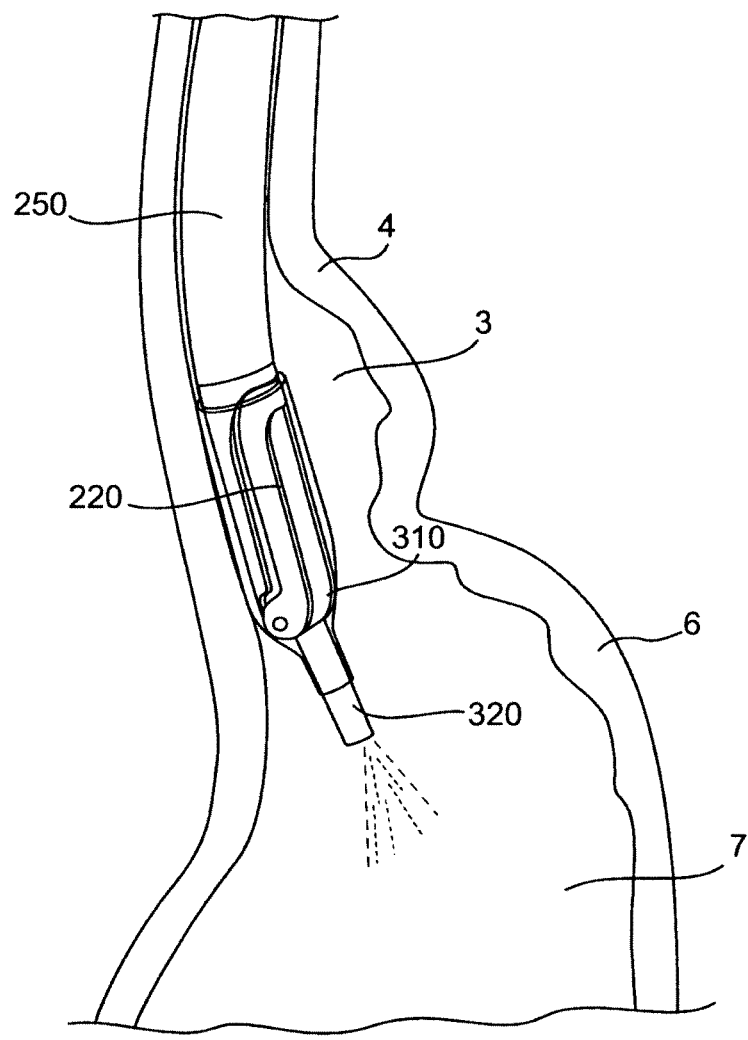
FIGS. 32 through 38 are schematic illustrations of a tissue invagination method, according to an embodiment of the present invention.

FIG. 32 illustrates the transoral insertion of the A-frame device 200 into the esophagus 3. During the insertion, a protective sleeve 310 is provided to cover the A-frame head 220. A suitable lubrication material may be applied on the outer or inner surface of the protective sleeve 310. The protective sleeve 310 protects the esophageal wall 4 from possible damage during the insertion. The protective sleeve 310 may have an opening in its distal end portion for an endoscope 320 to protrude out of the sleeve 310 for viewing. Other types of protective sleeves, such as the embodiments described in the commonly assigned U.S. application Ser. No. 09/920,809 of Yem Chin, filed on Aug. 3, 2001 and entitled "Protective Sleeve for an Endoscopic Instrument," and U.S. application Ser. No. 10/230,682 of Robert DeVries et al., filed on Aug. 29, 2002 and entitled "Devices and Methods for Fastening Tissue Layers," the disclosures of which are hereby incorporated by reference, may alternatively be utilized. Another protective sleeve embodiment, and embodiments of its method of manufacture and use, is shown in FIGS. 39-42D and described below.

Figure 33:
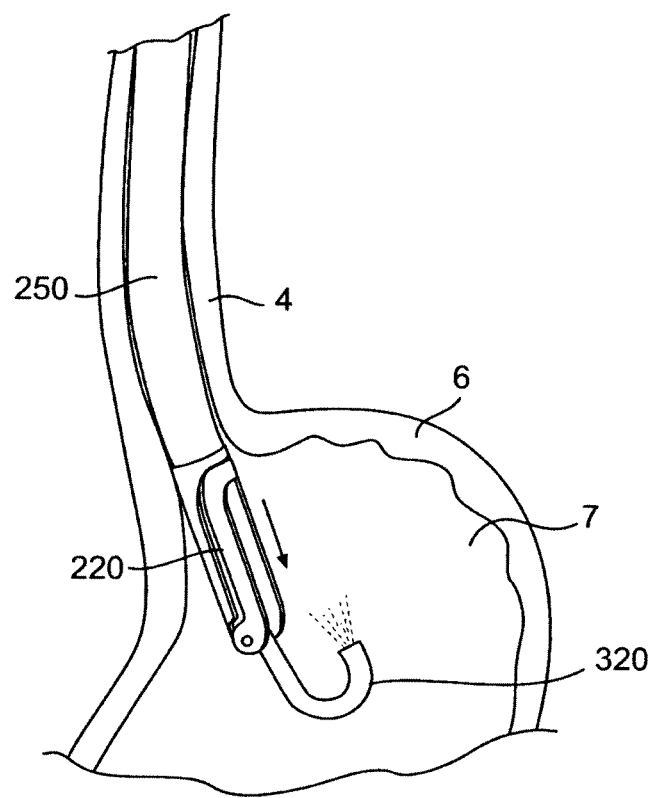

As shown in FIG. 33, once the A-frame head 220 is safely inserted into the gastro-esophageal junction site, the protective sleeve 310 is withdrawn from the A-frame head 220, for example, through a working channel of the A-frame device 200. This may be achieved by pulling a handle of the protective sleeve 310 proximally, causing the sleeve 310 to invert and move into the working channel where it is withdrawn. In an alternative embodiment, sleeve 310 has a tear strip or weakened portion, wherein removal of the sleeve is achieved by tearing open the sleeve. The sleeve may then fall into the gastrointestinal tract and pass normally. Such a sleeve may consist of biodegradeable material.

Figure 34:
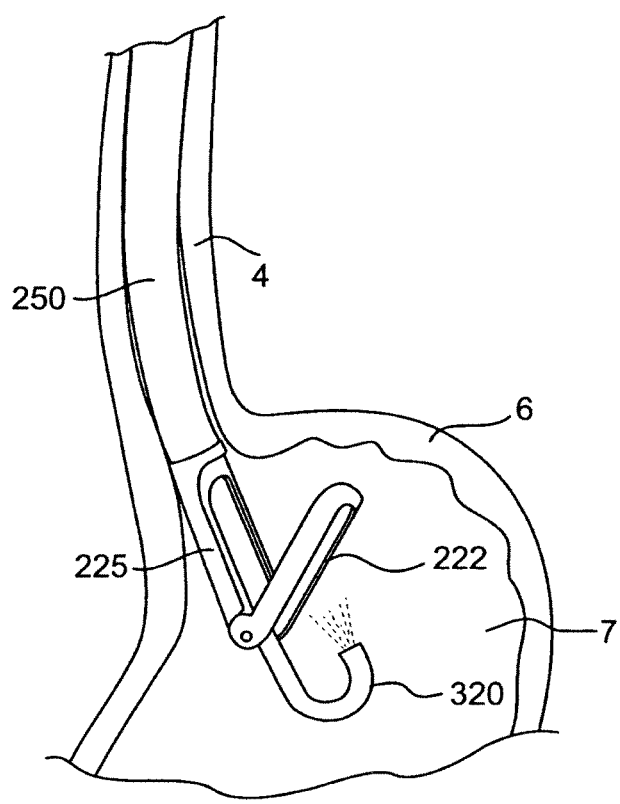

The endoscope 320 is then retroflexed in the stomach 7 to view the A-frame head 220 and the working area. Once the A-frame head 220 is positioned in the stomach 7, the folding arm 222 of the A-frame head 220 is opened by using the A-frame handle 280 on the proximal end of the downtube 250, as shown in FIG. 34. The A-frame head 220 is then lifted above the gastroesophageal junction towards the esophageal tissue.

Figure 35:
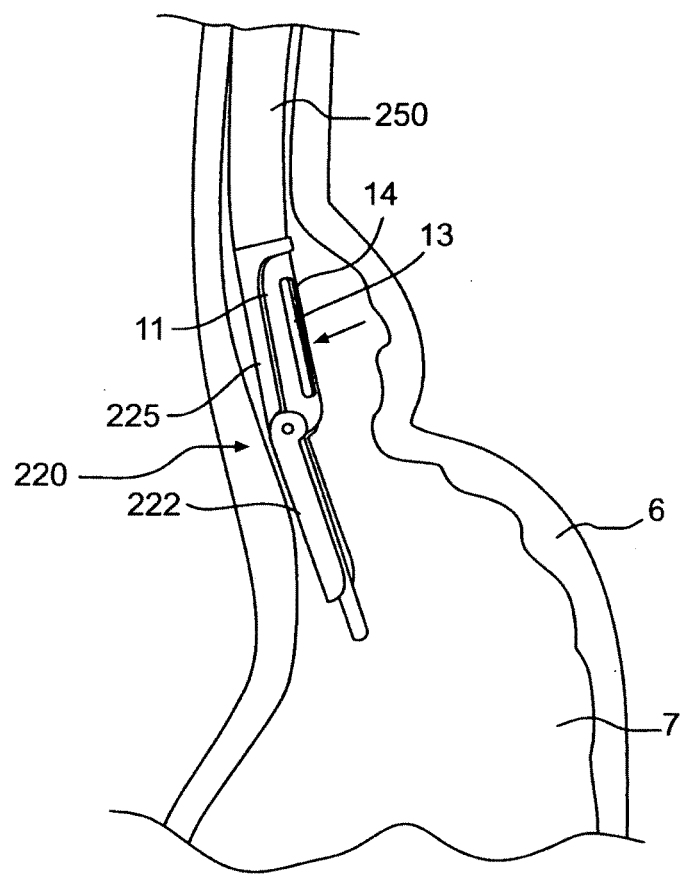
Figure 36:
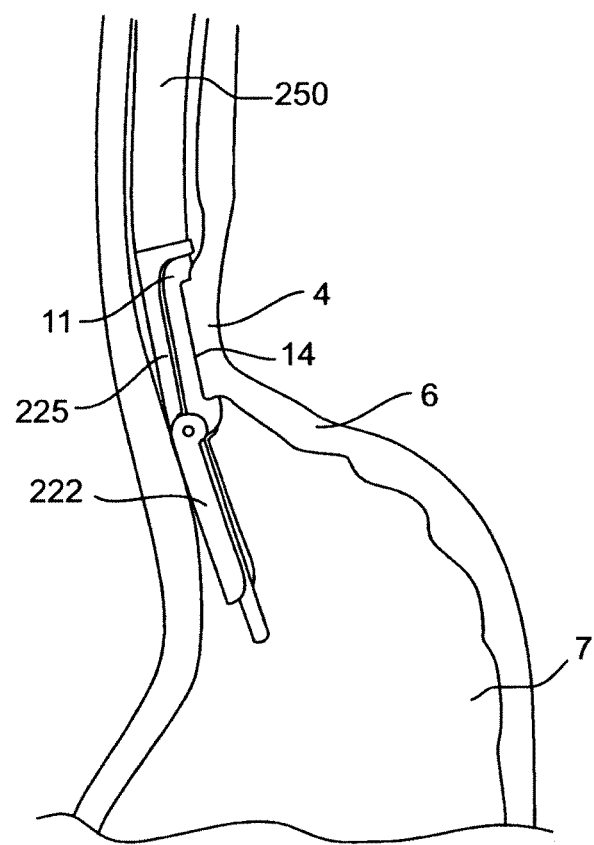
Figure 37:
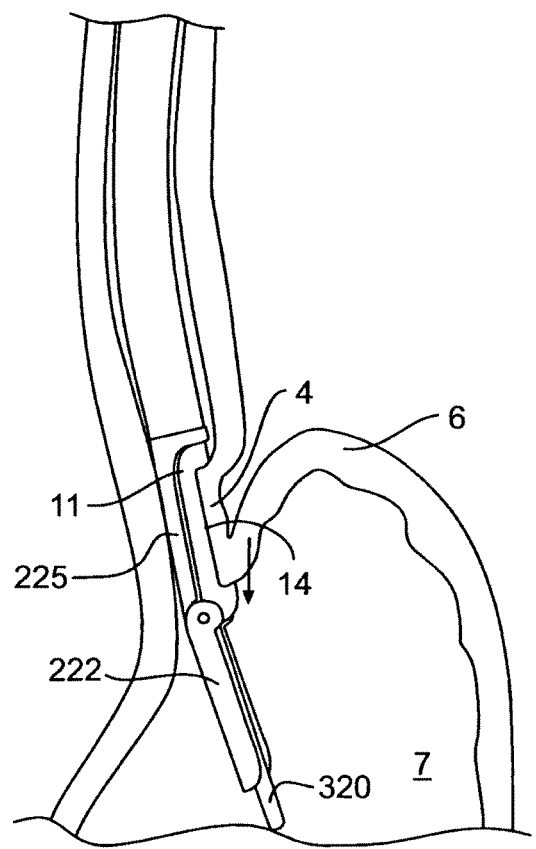
Figure 38:
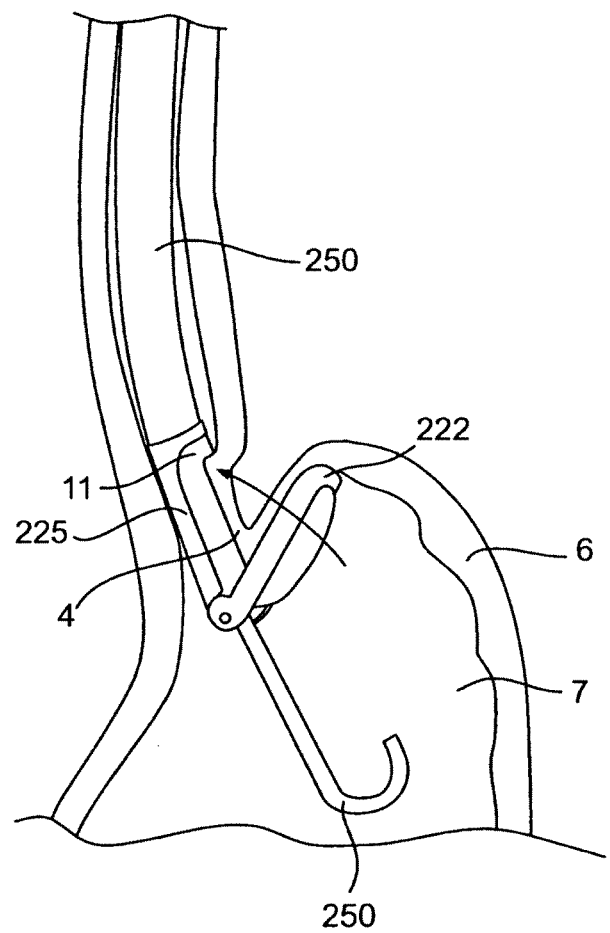

As shown in FIG. 35, when the A-frame head 220 is properly positioned proximate to the esophageal tissue, the invagination device 10, shown in FIGS. 4 and 5, is advanced into the A-frame downtube 250 and positioned proximate to the esophageal tissue to be invaginated. A vacuum source (not shown) is then turned on and the suction force is applied to firmly hold the esophageal tissue, as shown in FIG. 36. The holding of the esophageal tissue 4 can be enhanced by activation of a jaw assembly 14 placed in the vicinity of the suction opening 13 of the invagination head 11. When the jaw assembly 14 grasps the tissue 4, a suction may be continued or turned off, as desired. The firmly grasped esophageal tissue 4 is then pushed down toward the stomach 7, as indicated by an arrow shown in FIG. 37. As shown in FIG. 38, the folding arm 222 then closes to fold the fundus wall 6 proximate to the esophagus wall 4, creating a plicated fold 1, shown in FIGS. 2 and 3. Once the plicated fold 1 is firmly held by the folding arm 222, the vacuum source supplied to the invagination device 10 (if still applied) is turned off and the jaws are opened to release the grasped esophageal tissue, and the invagination device 10 is withdrawn from the A-frame device 200. A suitable tissue fastener may then be applied to the fold 1.

As an alternative embodiment, the A-frame device may be configured to also serve as the invagination device, eliminating the need for a separate invagination device during the procedure. As an example, the A-frame head may include a main body having a hollow portion. Ports in the main body may be placed in fluid communication with the hollow portion and a lumen in the downtube that communicates with a source of suction. With the folding arm open, the application of suction will grasp the esophagus. The entire device then may be pushed downward to invaginate the esophagus, and the arm folded to perform fundoplication. Suction may be applied during the folding to promote more accurate positioning. As a further alternative, various moving components of the disclosed A-frame devices, including especially components of the A-frame head, may be integrally manufactured, for example a living hinges.

Figure 39:
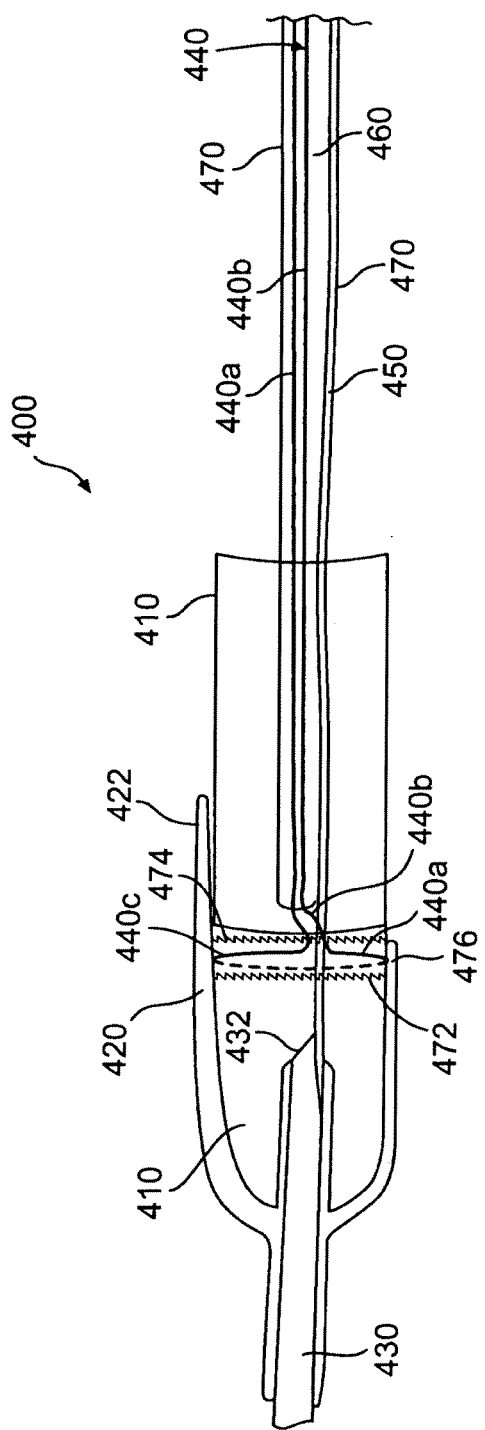
FIG. 39 is a side view of a protective sleeve, according to an embodiment of the present invention.

FIG. 39 shows an embodiment of a protective sleeve 400 that may be used in connection with an endoscopic device to protect an internal tissue tract, such as an esophagus, from damage as the endoscopic device is inserted into a patient. The components of sleeve 400 include an inner sleeve 410, an outer balloon 420, a distal tube 430, an inflation tube 450, an actuation tube 460, actuator wire 440, and an outer tube layer 470.

Distal tube 430 may consist of a semi-rigid tube having open proximal and distal ends and a lumen of sufficient diameter to accommodate an endoscope that may be used for imaging/visualization purposes. Tube 430 may include an angled, open proximal end to permit easier entry of an endoscope into tube 430 and easier withdrawal of sleeve 400 into the working channel of an endoscopic device, such as an A-frame device, being protected by sleeve 400. The angle of the proximal end of tube 430 relative to its longitudinal axis may be approximately 45 degrees. Tube 430 may be made of any suitable biocompatible material known in the art so that tube 430 has sufficient strength to permit access for an endoscope.

Balloon 420 connects to tube 430 proximate the proximal and distal ends of tube 430. Balloon 420 may be made of any suitable biocompatible material known in the art. Balloon 420 at least partially surrounds sleeve 410 and may include a tab 422 at its proximal end. Tab 422 may be manipulated by a user should it be desired to reuse sleeve 400 during an endoscopic operation. Tab 422 permits a user to easily grasp and pull balloon 420 distally to permit access to wire loop portion 440c. Upon access to wire loop portion 440c, the user may loosen the tension of portion 440c around sleeve 410 (i.e. uncinch the wire) and open sleeve 410 so that it may be replaced onto an endoscopic device.

Inflation tube 450 has a lumen in fluid communication with an interior of balloon 420. A distal end of tube 450 connects to balloon 420 at the proximal end of distal tube 430. A proximal end of tube 450 (not shown) may connect to any suitable source of inflation fluid and inflation actuation mechanism known in the art that may be used to supply inflation fluid, such as air, to balloon 420. Tube 450 may be made of any suitable material known in the art, such as polyethylene or other suitable polymers, and may have a length that approximates that of the endoscopic instrument that sleeve 400 is used with, for example approximately 60 cm.

Sleeve 410 may be made of balloon material, an extrusion material, or any other material sufficient to cover and protect the distal end of an endoscopic instrument from damaging a tissue tract during insertion. Balloon 420 is sealed to sleeve 410 along seals 472 and 474 that extend around the circumference of sleeve 410. Seals 472, 474 may be formed by any suitable method known in the art, such as heat treatment or adhesives, for example.

Figure 40:
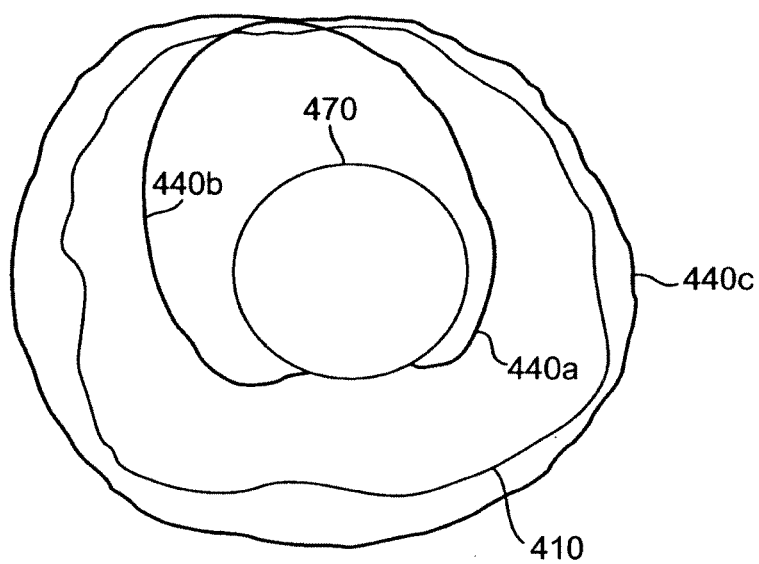
FIG. 40 is a schematic end view of a portion of the protective sleeve of FIG. 39.

Actuator wire 440 may be a single wire, cable, or like actuator. The ends of wire 440 remain at the proximal end of sleeve 400 (not shown) and may connect to a suitable handle or other actuation mechanism to permit the user to apply tension to the ends of wire 440. From its ends, wire 440 extends distally within a lumen of an actuation tube 460 (see wire portions 440a and 440b of wire 440), past a distal end of tube 460, to within sleeve 410. Wire portions 440a and 440b then exit through a hole 476 in sleeve 410 and form a loop portion 440c around an exterior of sleeve 410. FIG. 40 schematically shows, through an end view, the shape that wire 440 assumes when it exits the distal end of actuation tube 460 (which is covered by an outer tube layer 470, as described below). Wires 440a and 440b exit tube 460, cross one another proximate the hole 476 in sleeve 410, and then form loop portion 440c that surrounds sleeve 410.

Actuation tube 460 may be made of any suitable material known in the art, such as polyethylene or other suitable polymers, and may have a length that approximates that of the endoscopic instrument that sleeve 400 is used with, for example approximately 60 cm. Outer tube layer 470 may be a heat shrinkable tubing that covers both tube 450 and tube 460. As an alternative to tubes 450 and 460 and layer 470, any dual-lumen tube may be used for inflation of balloon 420 and actuation of wire 440.

Sleeve 400 may be constructed through any number and order of manufacturing steps desired. FIGS. 41A to 41D show various steps in an exemplary embodiment of the manufacture of sleeve 400. The steps and their order shown in these Figures and described below are exemplary only. Other methods of manufacturing may be used and the order of the steps shown in the Figures and described below may be changed.

Figure 41A:
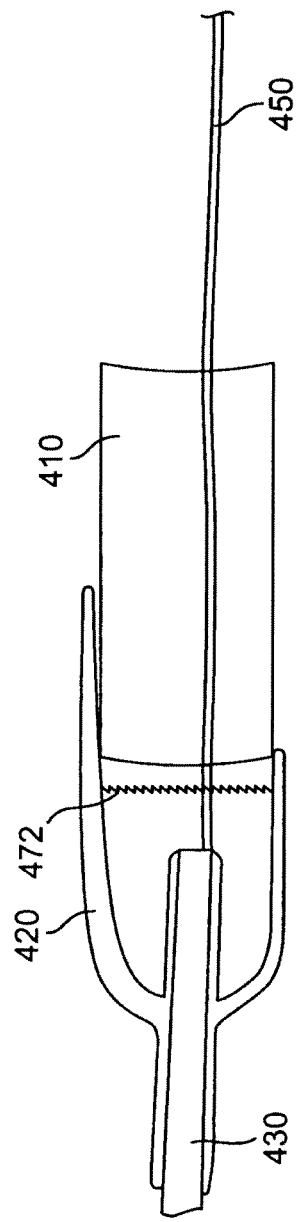

As shown in FIG. 41A, after both the distal tube 430 and the inflation tube 450 have been manufactured to the desired lengths, balloon 420 and tube 450 are affixed to tube 430 by an suitable connection means known in the art, including adhesives, heat treatment, etc. Sleeve 410 then is inserted over tube 450 and under balloon 420 and sealed to balloon 420 at seal 472. As mentioned above, seal 472 may extend around the circumference of sleeve 410 and be formed by any suitable method known in the art, such as heat treatment (e.g., soldering) or adhesives, for example.

As shown in FIG. 41B, hole 476 may be formed in sleeve 410, proximal to seal 472, by any suitable method known in the art, such as cutting or heat treatment, for example. Hole 476 may have a diameter of approximately 0.125 inches and may be formed at a point in sleeve 410 opposite tab 422 of balloon 420. Wire 440 then is positioned by inserting one end of wire 440 into hole 476 from within sleeve 410, wrapping wire 440 around sleeve 410 in the configuration shown in FIG. 40 to form wire loop portion 440c, and then placing the wire end back into hole 476 and into the interior of sleeve 410.

Figure 41C:
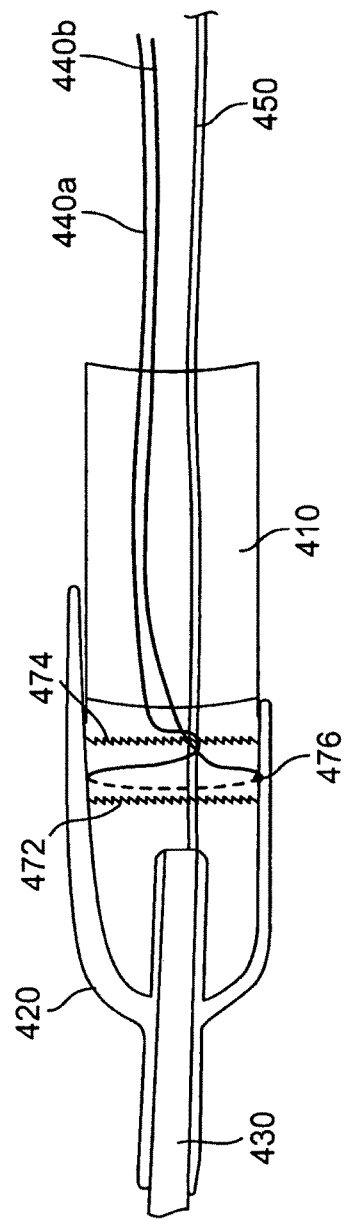

As shown in FIG. 41C, seal 474 between sleeve 410 and balloon 420 then is formed proximal to hole 476. As mentioned above, seal 474 may extend around the circumference of sleeve 410 and be formed by any suitable method known in the art, such as heat treatment (e.g., soldering) or adhesives, for example. Seal 474 aids in retaining wire 440 in place around sleeve 410. Also as shown in FIG. 41C, the open proximal end of tube 430 may be cut to a desired angle to permit easier entry of an endoscope into tube 430 and easier withdrawal of sleeve 400 into the working channel of an endoscopic device being protected by sleeve 400. Any suitable cutting method known in the art may be used to cut the proximal end of tube 430. The angle of the proximal end of tube 430 relative to its longitudinal axis may be cut to approximately 45 degrees and the cut may be made to line up with hole 476 and angled proximally toward the inflation tube 450 for easier withdrawal of sleeve 400 into the working channel of an endoscopic device.

Figure 41D:
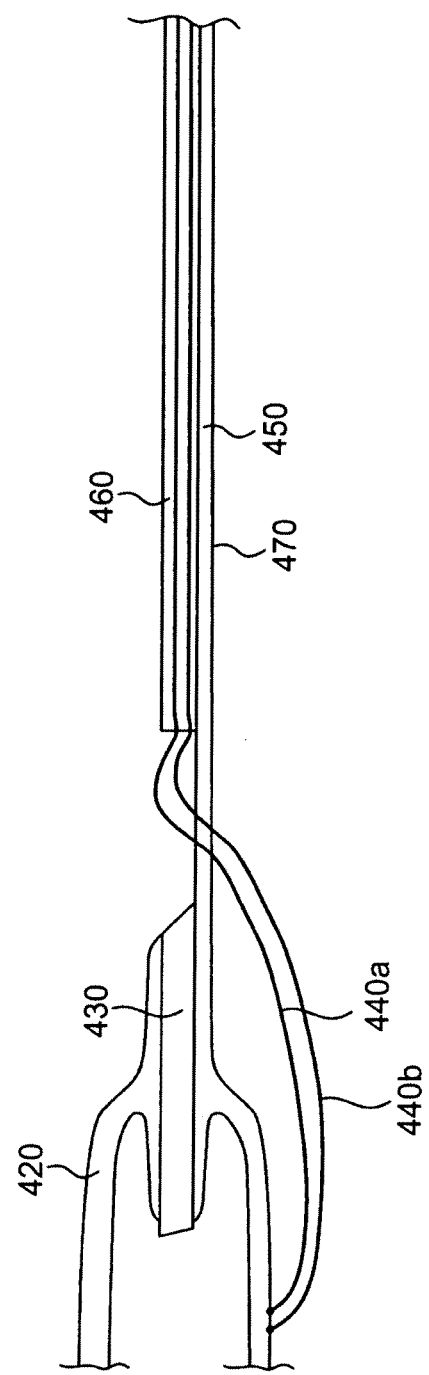

As shown in FIG. 41D, both ends of wire 440 are placed in actuation tube 460 and an outer tube layer 470, such as a heat shrinkable tubing, is placed around tubes 450 and 460. Alternatively, a heat shrinkable tubing may be placed around tubes 450 and 460 first, and then wire 440 inserted into the distal end of tube 460. A small hole may need to be made in the outer tube layer 470 at the distal end of tube 460 to permit insertion of the ends of wire 440. To perform these steps, balloon 420 and sleeve 410 may need to be moved in the distal direction to permit access to the distal end of actuation tube 460, as shown in FIG. 41D. The ends of wire 440 then are threaded to the proximal end of tube 460 and attached to a suitable actuation mechanism or handle (not shown).

FIGS. 42A-42D show certain steps in an embodiment of a method of using sleeve 400 in connection with an endoscopic procedure. These Figures and the description below show sleeve 400 used in connection with an A-frame device 200. Sleeve 400, however, may be used with any endoscopic device where protection of a patient's tissue tract from the distal end of the device during insertion is desirable. In addition, the method steps and their order shown in these Figures and described below are exemplary only. Other methods of use and the order of the steps shown in the Figures may be suitable.

As an initial step in the method of use, a user should make sure that wire loop portion 440c is open around sleeve 410. To loosen loop portion 440c, the user may lift tab 422 of balloon 420 and pull balloon 420 distally to permit access to wire 440. Upon access to wire 440, the user may loosen the tension of wire loop portion 440c and open sleeve 410.

Sleeve 400 then is backloaded through a working channel of A-frame device 200 until sleeve 400 is in the position shown in FIG. 42A. FIG. 42A shows a top view of A-frame head 220 of A-frame device 200 covered with sleeve 400. Sleeve 400, and particularly inflation tube 450, is placed in communication with a source of inflation fluid at the proximal end of tube 450. Balloon 420 then is inflated, as shown in FIG. 42B. FIG. 42B shows a side view of A-frame head 220 of A-frame device 200 covered with sleeve 400.

Protective sleeve 400 and A-frame device 200 then are inserted into a patient's tissue tract, such as an esophagus, until sleeve 410 and device 200 reach a desired position, such as that shown in FIG. 32. An endoscope may be used during insertion for visualization. The endoscope may be inserted through the working channel of A-frame device 200 and through distal tube 430 of sleeve 400. The endoscope may be placed in this position prior to insertion of device 200 and sleeve 400 into the patient.

Figure 42C:
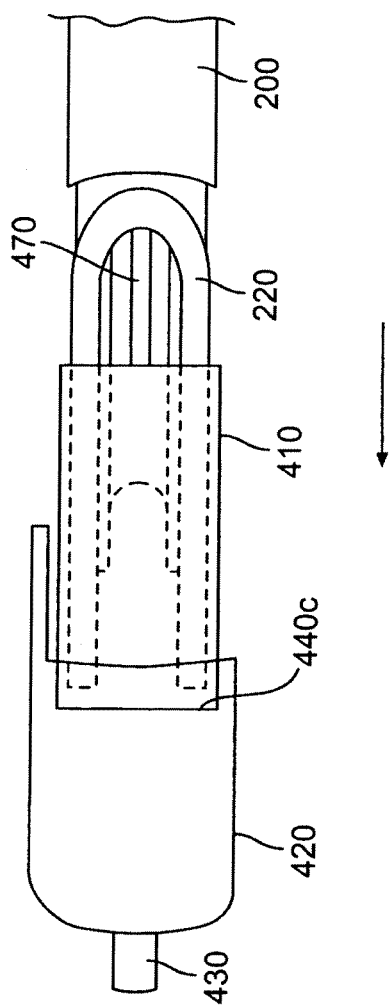
Figure 42D:
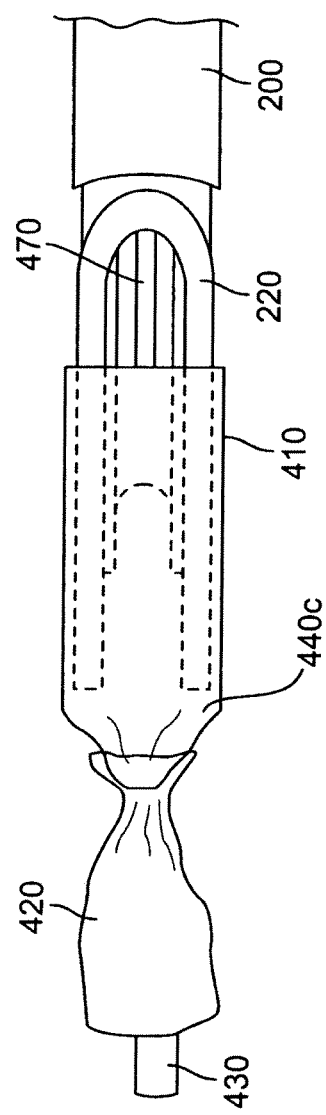

Once A-frame device 200 is in the desired position, the endoscope should be pulled proximally into the A-frame head 220 and balloon 420 deflated. Sleeve 400 then is advanced distally (as shown by the arrow in FIG. 42C) until wire loop portion 440c is distal to A-frame head 220. This position can be verified by use of the endoscope. As shown in FIG. 42D, wire loop portion 440c then is cinched around sleeve 410 by pulling on the ends of wire 440. Protective sleeve 400 then is pulled proximally into the A-frame head 220. Pulling proximally will invert balloon 420 and sleeve 410 and pull the protective sleeve 400 into the A-frame head 220. During this step, sleeve 410 will fold over balloon 420 to protect balloon 420 from puncture as it is removed from the A-frame device 200. Continued pulling of sleeve 400 will remove sleeve 400, including balloon 420 and sleeve 410, from the working channel of the A-frame device 200 and out of the patient.

Should it be desired to reuse sleeve 400 during the endoscopic operation, tab 422 may be manipulated by a user, as described above, to permit access to wire loop portion 440c and thereby loosen the tension of loop portion 440c around sleeve 410.

Although the present invention is depicted in this disclosure as being used in the treatment of GERD, e.g., a fundoplication procedure performed in the gastro-esophageal junction, it is to be understood that the invagination devices and related deployment methods of the present invention can be used in a variety of different types of surgical procedures.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A sheath for protecting tissue from an endoscopic instrument, the sheath comprising:
   a sleeve having a proximal end and a distal end;
   a tube extending from the distal end of the sleeve, wherein a lumen of the tube is in fluid communication with a lumen of the sleeve;
   an inflatable member surrounding an entire circumference of at least a portion of each of the tube and the sleeve, wherein the tube has a first diameter and the sleeve has a second diameter, and wherein the first diameter is less than the second diameter; and
   a flexible activation element around a circumference of the sleeve and extending proximally through the sleeve and, through proximal retraction of the activation element, the sleeve is deformed and configured to be withdrawn through a channel of the endoscopic instrument.

2. The sheath of claim 1, further including a flexible elongate member configured to form a loop around the sleeve.

3. The sheath of claim 2, wherein the tube is a first tube, wherein the sheath further comprises a second tube extending from the proximal end of the sleeve, and wherein the flexible elongate member includes a first portion and a second portion, and wherein the first and second portions extend through a lumen in the second tube.

4. The sheath of claim 2, wherein the flexible elongate member is configured to have a loose configuration such that an endoscopic instrument may move within the sheath, and a tight configuration such that an endoscopic instrument may be substantially secured within the sheath.

5. The sheath of claim 1, wherein the inflatable member includes an extension movable distally relative to the sleeve.

6. The sheath of claim 1, wherein the inflatable member is an inflatable member connected to an inflation tube.

7. The sheath of claim 6, wherein the inflation tube extends through the proximal end of the sleeve and connects to the inflatable member at a proximal end of the tube.

8. The sheath of claim 1, wherein the sheath is configured to at least partially contract around an endoscopic instrument.

9. The sheath of claim 8, wherein a flexible elongate member controls the contraction of the sheath around the endoscopic instrument.

10. The sheath of claim 9, wherein the flexible elongate member is configured to follow a path through a lumen in the sleeve, through an opening in an exterior surface of the sleeve, and around the exterior surface of the sleeve.

11. The sheath of claim 1, wherein the sheath is mounted on an exterior surface of the endoscopic instrument.

12. A sheath for protecting tissue from an endoscopic instrument, the sheath comprising:
   a sleeve having a proximal end and a distal end;
   a tube having a proximal end and a distal end, wherein the proximal end of the tube is located within a lumen in the sleeve, and the distal end of the tube extends from the distal end of the sleeve;
   an expandable member at least partially surrounding the tube and the sleeve; and
   a flexible activation element around a circumference of the sleeve and extending proximally through the sleeve and, through proximal retraction of the activation element, the sleeve is deformed and configured to be withdrawn through a channel of the endoscopic instrument.

13. The sheath of claim 12, wherein the tube has a length extending from the proximal end of the tube to the distal end of the tube, and wherein the expandable member substantially surrounds the tube along the length.

14. The sheath of claim 12, wherein the proximal end of the tube has an angled opening.

15. The sheath of claim 12, wherein the expandable member includes a first configuration in which the expandable member substantially surrounds the loop, and a second configuration in which the expandable member does not substantially surround the loop.

16. The sheath of claim 15, wherein the expandable member is configured to transition between the first and second configurations via an extension on the expandable member.

17. The sheath of claim 12, wherein the expandable member is at least partially fixed to the sleeve.

18. The sheath of claim 12, wherein the flexible elongate member has a first portion and a second portion, and wherein the first and second portions are at least partially within the sleeve.

19. A sheath for protecting tissue from an endoscopic instrument, the sheath comprising:
   an inner sleeve having a proximal end and a distal end;
   a tube extending from the distal end of the sleeve;
   an inflatable portion at least partially surrounding the tube and at least partially surrounding the sleeve;
   an inflation lumen connected to the inflation portion and extending proximally through the proximal end of the sleeve; and
   a flexible activation element forming a loop around the sleeve and extending proximally through the proximal end of the sleeve, wherein the loop contacts the sleeve and is capable of changing diameters through proximal retraction of the activation element, wherein the sleeve is deformable and configured to be withdrawn through a channel of the endoscopic instrument.

* * * * *